United States Patent
Misu et al.

(10) Patent No.: US 10,759,424 B2
(45) Date of Patent: Sep. 1, 2020

(54) VEHICLE DATA SELECTION SYSTEM FOR MODIFYING AUTOMATED DRIVING FUNCTIONALITIES AND METHOD THEREOF

(71) Applicant: Honda Motor Co., Ltd., Tokyo (JP)

(72) Inventors: Teruhisa Misu, Mountain View, CA (US); Nanxiang Li, San Mateo, CA (US); Ashish Tawari, Santa Clara, CA (US)

(73) Assignee: HONDA MOTOR CO., LTD., Tokyo (JP)

( * ) Notice: Subject to any disclaimer, the term of this patent is extended or adjusted under 35 U.S.C. 154(b) by 247 days.

(21) Appl. No.: 15/238,045

(22) Filed: Aug. 16, 2016

(65) Prior Publication Data

US 2018/0050696 A1 Feb. 22, 2018

(51) Int. Cl.
*G06F 17/00* (2019.01)
*B60W 30/14* (2006.01)
*G07C 5/08* (2006.01)
*A61B 5/00* (2006.01)
*A61B 5/0205* (2006.01)

(Continued)

(52) U.S. Cl.
CPC ........... *B60W 30/14* (2013.01); *A61B 5/0077* (2013.01); *A61B 5/02055* (2013.01); *A61B 5/18* (2013.01); *A61B 5/4803* (2013.01); *A61B 5/6893* (2013.01); *A61B 5/7282* (2013.01); *B60W 40/09* (2013.01); *B60W 50/12* (2013.01); *G07C 5/008* (2013.01); *G07C 5/0841* (2013.01); *A61B 5/024* (2013.01); *B60W 2040/0818* (2013.01); *B60W 2040/0872* (2013.01); *B60W 2050/0088* (2013.01); *B60W 2050/0089* (2013.01); *B60W 2540/22* (2013.01); *B60W 2556/45* (2020.02)

(58) Field of Classification Search
CPC ...... B60W 30/14; B60W 40/09; B60W 50/12; B60W 2040/0818; B60W 2040/0872; A61B 5/0077; A61B 5/02055; A61B 5/18; A61B 5/4803; A61B 5/6893; A61B 5/7282; A61B 5/024; G07C 5/008; G07C 5/0841
USPC .......................................................... 701/48
See application file for complete search history.

(56) References Cited

U.S. PATENT DOCUMENTS 8,874,301 B1 10/2014 Rao et al.
9,135,803 B1 9/2015 Fields et al.
(Continued)

OTHER PUBLICATIONS

International Search Report of related International Patent Application No. PCT/US2017/042845, dated Sep. 29, 2017.
(Continued)

*Primary Examiner* — Ronnie M Mancho
(74) *Attorney, Agent, or Firm* — Arent Fox, LLP

(57) ABSTRACT

The systems and methods provided herein are directed to the uploading and transmission of vehicle data to a remote system when a physiological event for a driver has been detected using one or more sensors. Information such as the driver's heart rate, temperature, voice inflection or facial expression may be monitored to detect the physiological event. Vehicle data, such as gathering or control system data, may be sent once the event has been detected. Selected vehicle data associated with the event or all data during the time of the event may be sent. After receiving the vehicle data, the remote system may process or store it where it may be used to modify automated driving functionalities.

22 Claims, 12 Drawing Sheets

(51) Int. Cl.
*A61B 5/18* (2006.01)
*B60W 40/09* (2012.01)
*B60W 50/12* (2012.01)
*G07C 5/00* (2006.01)
*B60W 50/00* (2006.01)
*A61B 5/024* (2006.01)
*B60W 40/08* (2012.01)

(56) References Cited

U.S. PATENT DOCUMENTS

| | | | | |
|---|---|---|---|---|
| 9,767,516 | B1* | 9/2017 | Konrardy | G06Q 40/08 |
| 2004/0225557 | A1 | 11/2004 | Phelan et al. | |
| 2008/0252487 | A1* | 10/2008 | McClellan | G01S 5/0027 |
| | | | | 340/936 |
| 2008/0294690 | A1* | 11/2008 | McClellan | G01S 5/0027 |
| 2013/0073112 | A1* | 3/2013 | Phelan | G06Q 40/00 |
| | | | | 701/1 |
| 2013/0289821 | A1 | 10/2013 | Nakagawa | |
| 2014/0113619 | A1 | 4/2014 | Tibbitts et al. | |
| 2014/0222245 | A1 | 8/2014 | Chang | |
| 2014/0309849 | A1 | 10/2014 | Ricci | |
| 2014/0309864 | A1* | 10/2014 | Ricci | H04W 4/21 |
| | | | | 701/36 |
| 2015/0005608 | A1* | 1/2015 | Evans | A61B 5/0428 |
| | | | | 600/383 |
| 2015/0053066 | A1* | 2/2015 | Hampiholi | B60W 50/14 |
| | | | | 84/602 |
| 2015/0062168 | A1* | 3/2015 | Ng-Thow-Hing | G02B 27/01 |
| | | | | 345/633 |
| 2015/0100179 | A1* | 4/2015 | Alaniz | A63F 13/00 |
| | | | | 701/1 |
| 2015/0216466 | A1 | 8/2015 | Kronberg et al. | |
| 2015/0229341 | A1* | 8/2015 | Fung | H04B 1/10 |
| | | | | 702/191 |
| 2015/0254955 | A1 | 9/2015 | Fields et al. | |
| 2015/0367780 | A1 | 12/2015 | Hilsebecher et al. | |
| 2016/0001781 | A1* | 1/2016 | Fung | G06F 19/345 |
| | | | | 701/36 |
| 2016/0061613 | A1* | 3/2016 | Jung | G01C 21/3632 |
| | | | | 701/49 |
| 2016/0104486 | A1* | 4/2016 | Penilla | H04L 67/12 |
| | | | | 704/232 |
| 2016/0107509 | A1* | 4/2016 | Kirsch | B60H 1/00742 |
| | | | | 165/202 |
| 2016/0152180 | A1* | 6/2016 | Kirsch | B60Q 9/00 |
| | | | | 701/36 |
| 2016/0176409 | A1* | 6/2016 | Kirsch | B60W 40/08 |
| | | | | 701/37 |
| 2016/0321599 | A1* | 11/2016 | Baughman | G06Q 10/06311 |
| 2017/0102700 | A1* | 4/2017 | Kozak | B60W 30/00 |
| 2017/0232297 | A1* | 8/2017 | Prokhorov | A63B 24/0075 |
| | | | | 482/8 |
| 2017/0303332 | A1* | 10/2017 | Yuan | H04W 76/026 |
| 2017/0316463 | A1* | 11/2017 | Pielot | G06Q 30/0269 |
| 2018/0004211 | A1* | 1/2018 | Grimm | G05D 1/0214 |
| 2018/0032825 | A1* | 2/2018 | Fung | G06K 9/00845 |
| 2018/0043901 | A1* | 2/2018 | Kim | H04W 4/029 |
| 2018/0093675 | A1* | 4/2018 | Holub | A61B 5/02405 |
| 2018/0103022 | A1* | 4/2018 | Tokunaga | H04L 63/20 |
| 2018/0118219 | A1* | 5/2018 | Hiei | B60W 40/09 |
| 2018/0126951 | A1* | 5/2018 | Ricci | B60R 25/2018 |

OTHER PUBLICATIONS

Written Opinion of the International Searching Authority of related International Application No. PCT/US2017/042845, dated Sep. 29, 2017.

* cited by examiner

SELECTIVE SENDING

| PHYSIOLOGICAL EVENT | GATHERING SYSTEMS | CONTROL SYSTEMS |
|---|---|---|
| HEART RATE (NORMAL) | — | — |
| HEART RATE (STRESSED) | CAMERA, LIDAR/RADAR, GPS, MICROPHONE | TELECOMMUNICATION SYSTEM, STEERING SYSTEM, BLIND SPOT SYSTEM COLLISION WARNING SYSTEM |
| TEMPERATURE INCREASE | CAMERA, LIDAR/RADAR, GPS | CLIMATE CONTROL SYSTEM STEERING SYSTEM, BLIND SPOT SYSTEM COLLISION WARNING SYSTEM ACCELERATION/BRAKE SYSTEM |
| VOICE INFLECTION | MICROPHONE | TELECOMMUNICATION SYSTEM |
| FACIAL EXPRESSION (NERVOUS) | CAMERA, GPS | STEERING SYSTEM, BLIND SPOT SYSTEM, COLLISION WARNING SYSTEM, ACCELERATION/BRAKE SYSTEM, LANE ASSIST SYSTEM |
| FACIAL EXPRESSION (HAPPY) | — | — |
| FACIAL EXPRESSION (INTOXICATED) | GPS | — |

FIG. 16

VEHICLE DATA SELECTION SYSTEM FOR MODIFYING AUTOMATED DRIVING FUNCTIONALITIES AND METHOD THEREOF

BACKGROUND

Highly automated driving functions may or soon will be available for freeways and urban environments. These functions may rely on collected data received from vehicles on the road. Once collected, the data may be provided to a remote system for analysis, including annotations and markups. Uploading all data to the remote system, however, may not be possible. The size of the data may be too large. Furthermore, transmitting the data may be costly. The present disclosure provides a system and method thereof that addresses these concerns. Other benefits and advantages will become clear from the disclosure provided herein and those advantages provided are for illustration.

BRIEF DESCRIPTION

According to one exemplary embodiment, a vehicle having at least one automated driving functionality is provided. The vehicle may include at least one system receiving vehicle data, at least one sensor detecting a physiological event of a driver, and an interface providing the vehicle data to a remote system when the physiological event is detected, the interface receiving modifications based on the vehicle data to the at least one automated driving functionality from the remote system.

According to another exemplary embodiment, a method for providing vehicle data to a remote system is provided. The method may include receiving vehicle data from at least one system, detecting physiological information of a driver and providing the vehicle data to the remote system when an event is determined from the physiological information of the driver.

According to yet another exemplary embodiment, an in-vehicle computing system is provided. The system may include a physiological sensor, at least one processor and a memory operatively coupled to the processor, the memory storing program instructions that when executed by the processor, causes the processor to perform processes. The processes may include receiving vehicle data, detecting an event of a driver through the physiological sensor, providing a data window of vehicle data when the event is detected to a remote system and receiving at least one modification from the remote system to adjust an automated driving functionality.

BRIEF DESCRIPTION OF DRAWINGS

The novel features believed to be characteristic of the disclosure are set forth in the appended claims. In the descriptions that follow, like parts are marked throughout the specification and drawings with the same numerals, respectively. The drawing FIGURES are not necessarily drawn to scale and certain FIGURES may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 16 is an illustrative table depicting gathering and control system data to be uploaded based on detected physiological events in accordance with one aspect of the present disclosure.

DESCRIPTION OF THE DISCLOSURE

Figure 1:
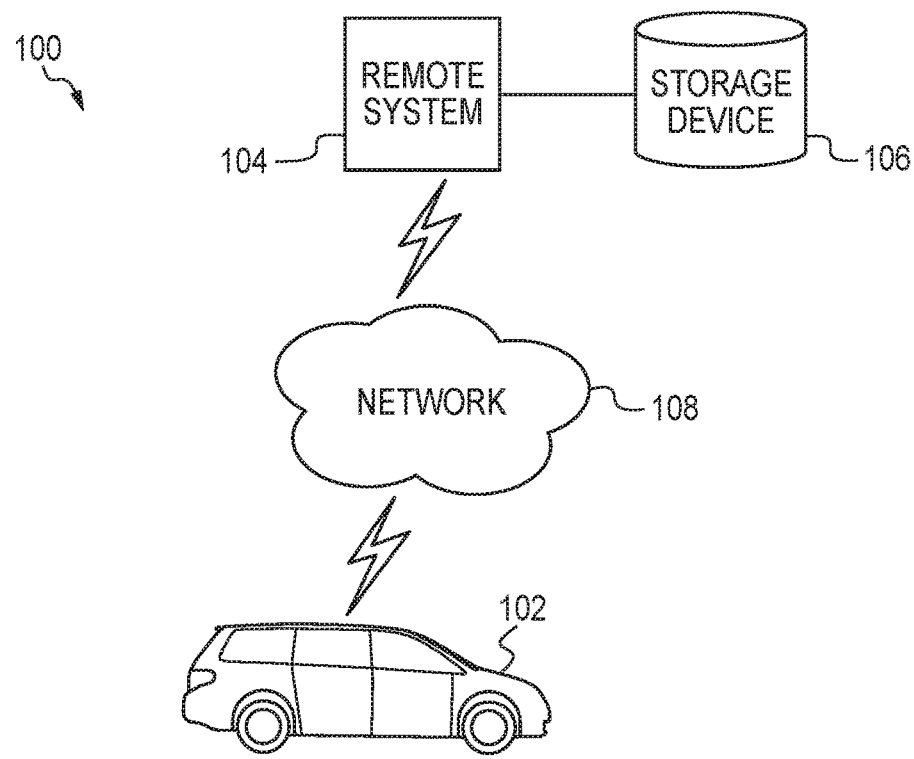
FIG. 1 is a schematic diagram of an illustrative environment for selectively uploading vehicle data in accordance with one aspect of the present disclosure.

The description set forth below in connection with the appended drawings is intended as a description of exemplary embodiments of the disclosure and is not intended to represent the only forms in which the present disclosure may be constructed and/or utilized. The description sets forth the functions and the sequence of blocks for constructing and operating the disclosure in connection with the illustrated embodiments. It is to be understood, however, that the same or equivalent functions and sequences may be accomplished by different embodiments that are also intended to be encompassed within the spirit and scope of this disclosure.

The following includes definitions of selected terms employed herein. The definitions include various examples and/or forms of components that fall within the scope of a term and that may be used for implementation. The examples are not intended to be limiting.

A "bus," as used herein, refers to an interconnected architecture that is operably connected to other computer components inside a computer or between computers. The bus may transfer data between the computer components. The bus may be a memory bus, a memory controller, a peripheral bus, an external bus, a crossbar switch and/or a local bus, among others.

"Computer communication," as used herein, refers to a communication between two or more computing devices (e.g., computer, personal digital assistant, cellular telephone, network device) and may be, for example, a network transfer, a file transfer, an applet transfer, an email, a hypertext transfer protocol (HTTP) transfer and so on. A computer communication may occur across, for example, a wireless system (e.g., IEEE 802.11), an Ethernet system (e.g., IEEE 802.3), a token ring system (e.g., IEEE 802.5), a media oriented system transport network (MOST), a local area network (LAN), a wide area network (WAN), a point-to-point system, a circuit switching system, a packet switching system, among others.

A "component," as used herein, includes, but is not limited to, non-transitory computer readable medium that stores instructions, instructions in execution on a machine, hardware, firmware, software in execution on a machine and/or combinations of each to perform a function(s) or an action(s) and/or to cause a function or action from another component, method and/or system. A component may also include logic, a software controlled microprocessor, a discrete logic circuit, an analog circuit, a digital circuit, a programmed logic device, a memory device containing executing instructions, logic gates, a combination of gates and/or other circuit components. Multiple components may be combined into one component and single components may be distributed among multiple components.

A "processor," as used herein, includes, but is not limited to a device that may process signals and perform general computing and arithmetic functions. Signals processed by the processor may include digital signals, data signals, computer instructions, processor instructions, messages, a bit, a bit stream or other means that may be received, transmitted and/or detected. Generally, the processor may be a variety of various processors including multiple single and multicore processors and co-processors and other multiple single and multicore processor and co-processor architectures. The processor may include various components to execute various functions.

A "memory," as used herein, may include volatile memory and/or non-volatile memory. Non-volatile memory may include, for example, ROM (read only memory), PROM (programmable read only memory), EPROM (erasable PROM) and EEPROM (electrically erasable PROM). Volatile memory may include, for example, RAM (random access memory), synchronous RAM (SRAM), dynamic RAM (DRAM), synchronous DRAM (SDRAM), double data rate SDRAM (DDR SDRAM) and direct RAM bus RAM (DRRAM). The memory may store an operating system that controls or allocates resources of a computing device. Memory may be operatively coupled to the processor. The memory may store program instructions that may be executed by the processor.

A "disk," as used herein, may be a magnetic disk drive, a solid state disk drive, a floppy disk drive, a tape drive, a Zip drive, a flash memory card and/or a memory stick. Furthermore, the disk may be a CD-ROM (compact disk ROM), a CD recordable drive (CD-R drive), a CD rewritable drive (CD-RW drive) and/or a digital video ROM drive (DVD ROM) or the media associated with such drives. The disk may store an operating system that controls or allocates resources of a computing device.

An "operable connection" or a connection by which entities are "operably connected" or "communicably connected," as used herein, is one in which signals, physical communications and/or logical communications may be sent and/or received. An operable connection may include a wireless interface, a physical interface, a data interface and/or an electrical interface.

Generally described, the systems and methods provided herein are directed to the uploading and transmission of vehicle data to a remote system when a physiological event for a driver has been detected using one or more sensors. Information such as the driver's heart rate, temperature, voice inflection or facial expression may be monitored to detect the physiological event. Vehicle data, such as gathering or control system data, may be sent once the event has been detected. Selected vehicle data associated with the event or all data during the time of the event may be sent. After receiving the vehicle data, the remote system may process or store it where it may be used to modify automated driving functionalities.

Automated driving functionalities may be modified based on the received vehicle data sent after the event has been detected by the physiological sensor. These functionalities may be adjusted on the vehicle itself sending the vehicle data. Typically, the modifications may be made on a number of parameters or other settings on the vehicle. For example, the functionalities may include setting distances for an adaptive cruise control (ACC) system. Other functionalities that may be changed include adjusting the parameters for semi-autonomous or autonomous vehicles such as the level of aggressive driving style. The parameters or settings may be used to modify take over controls in autonomous vehicles. These controls are used, in some vehicles, to alert the driver that they should take over the steering wheel of the vehicle. The period of time may be adjusted depending on the received vehicle data. Over the air updates may be used to adjust the parameters or settings within the vehicle.

Alternatively, and after the vehicle data has been provided to the remote system, automated driving functionalities may be adjusted and processed for other vehicles, including future models. The functionalities would not be sent back to the vehicle; rather they would be used for other vehicles, including non-autonomous, semi-autonomous or autonomous vehicles. These functionalities may be characterized with new hardware and/or software that may be implemented within the other vehicles. For example, vision processing techniques may be updated on future vehicles that require both newer hardware and software. Lidar and/or radar may be used in conjunction with detection software. Positions of sensors may also be modified in future vehicles based on the received vehicle data. Another example of using the vehicle data to modify the driving functionality on other or future vehicles may include ACC systems or take over controls. Take over controls may be modified on future vehicles to provide a more ergonomic take over such as removing the use of a steering wheel and providing knobs or other buttons. Further examples will be provided below and these should not be construed as limiting.

As described above, the vehicle data along with the physiological event sent from the vehicle may be processed to derive information including modifying driving functionalities. In one illustration, vehicle data such as captured images may be analyzed at the remote system and annotated after the driver has been determined to be nervous. Annotations, such as labeling, may be performed through manual or automated software. These labels may provide training models in machine learning algorithms for automated driving functionalities.

To provide a further clarifying example, lane line images may be captured to train a learning algorithm. Images of the lanes may define broken, solid, double or dashed lanes, for example. The nervousness of the driver, possibly due to these lane lines, may be detected by a physiological sensor and noted as an event. Camera feeds or seat sensors may be used to detect the event. When the event is detected, the lane line images may be provided to the remote system. Global position system (GPS) coordinates, which may be used to define the vehicle's position and a form of vehicle data, may also be sent in addition to the lane line images to the remote system for processing. Automated driving functionalities may then use the results of the processing by the remote system, for example, issues within the lane may be determined. These issues may include, but are not limited to, unpainted lines or unevenly spaced lines. These issues with the lanes may cause the vehicle to use different systems to determine whether the vehicle is still within the lane, for example, using a differential global positioning system (DGPS) may be used instead of the captured images.

In another example, vehicle data such as automated cruise control system information may be provided to the remote system when a physiological sensor in the vehicle detects a change in facial expressions of the driver. The physiological sensors in the vehicle may detect that the driver is anxious as a triggering event to provide the automated cruise control system information. The vehicle data may include distance information at which the automated cruise control system was set. The remote system may process this information and determine that the driver's car was too close, and the distance should be increased such that the driver would feel more comfortable using this functionality.

In yet another example, vehicle data in the form of acceleration and braking information may be provided to the remote system when a driver's heart rate triggers a physiological event. The event may be caused by a sharp increase to the driver's heart rate. The vehicle data may then be processed by the remote system to understand driving behaviors to adjust automated driving functionalities, for example, when the driver is aggressive, the system may note that the driver likes to drive in a certain fashion and may adjust the driving of the semi-autonomous or autonomous automated driving functionalities to fit with their behavior.

In another example, a physiological event of a driver's temperature reaching below a threshold may cause the vehicle to send vehicle data in the form of takeover data to the remote system. The decrease of temperature may be used to determine whether a driver is sleeping as a driver's body temperature decreases in such a state. The information may be used by the remote system to determine the appropriate amount of time for signaling to a driver to wake up and take control of the vehicle. Automated driving functionalities may be modified based on this information.

In one example, vehicle data such as GPS coordinates may be provided to the remote system when the driver has been detected to be intoxicated. The GPS coordinates may be sent to the remote system where automated driving functionalities may be processed and then sent back to the vehicle such that the vehicle may be pulled to an exit and parked safely around the provided GPS coordinates.

As shown above, a number of examples were discussed that caused the vehicle to provide vehicle data based on a physiological event of the driver. The data would then be processed on the remote system to adjust automated driving functionalities. The remote system would use this data to modify these functionalities. The modifications may be communicated back to the vehicle or may be used by those working on these automated driving functionalities for future semi-autonomous or autonomous vehicles. These examples should not be construed as limiting. Rather, multiple examples may be derived from those given above as well as those that will be presented below Turning to FIG. 1, a schematic diagram of an illustrative environment 100 for selectively uploading vehicle data in accordance with one aspect of the present disclosure is provided. The environment 100 may include a vehicle 102, remote system 104 and optional storage device 106 coupled to the remote system 104. The vehicle 102 and remote system 104 may be communicatively connected with one another through a communications network 108. The environment 100 may include fewer or more components and is not limited by those shown.

The vehicle 102 may include a non-autonomous, semi-autonomous or autonomous vehicle. While shown as a car, the vehicle 102 may also be a motorcycle, truck, bus, airplane, boat or other similar transportation vehicle. The vehicle 102 may be travelling while vehicle data is being gathered. This includes while the vehicle 102 may be stopped in traffic.

The remote system 104 may be hosted on a server or other platform. The remote system 104 may be communicatively coupled to a storage device 106 either directly or indirectly, for example, over the communications network 108 or other internal network. The storage device 106 of the remote system 104 may be internal or external to the remote system 104. The storage device 106 may hold or retain vehicle data. The physiological event that led to the vehicle data uploading may be saved with that vehicle data in the storage device 106. The vehicle data along with the event may be accessed in real time or at a future time.

The communications network 108 may include or take the form of one or more wired and/or wireless networks. The network 108 may include one or more wide area networks such as the Internet or a portion thereof, one or more cellular networks, one or more telephone networks, various intermediate networking devices and edge devices such as wireless and/or wired access points, etc. Wireless access points may support the same or different wireless communications protocols. As one example, wireless access points may each support communications over wide-area cellular network protocols. As another example, wireless access point may support communications over a local-area network using the Wi-Fi protocol, while wireless access point may support communications over a wide-area cellular network.

Wireless communications between two or more devices within the environment 100 may take the form of short-range wireless communications link utilizing near-field communications or a personal area network via an RFID protocol, the Bluetooth® wireless communication protocol, the Wi-Fi wireless communication protocol or other suitable wireless communication protocol. In addition, wireless communications between the components of the environment 100 may be provided over a local area network and/or a wide area network using other suitable protocols and may traverse one or more intermediate networking devices and/or access points. For example, wireless links may utilize GSM, 3G UMTS/3GPP and/or 4G LTE/3GPP cellular protocols, Wi-Fi 802.11 protocols as defined by IEEE, Wi-Max 802.16 protocols as defined by IEEE or other suitable wireless communication protocols. For example, communication flows in association with the communications network 108 may take the form of relatively long-range wireless communications using one or more of these wireless communication protocols.

Figure 2:
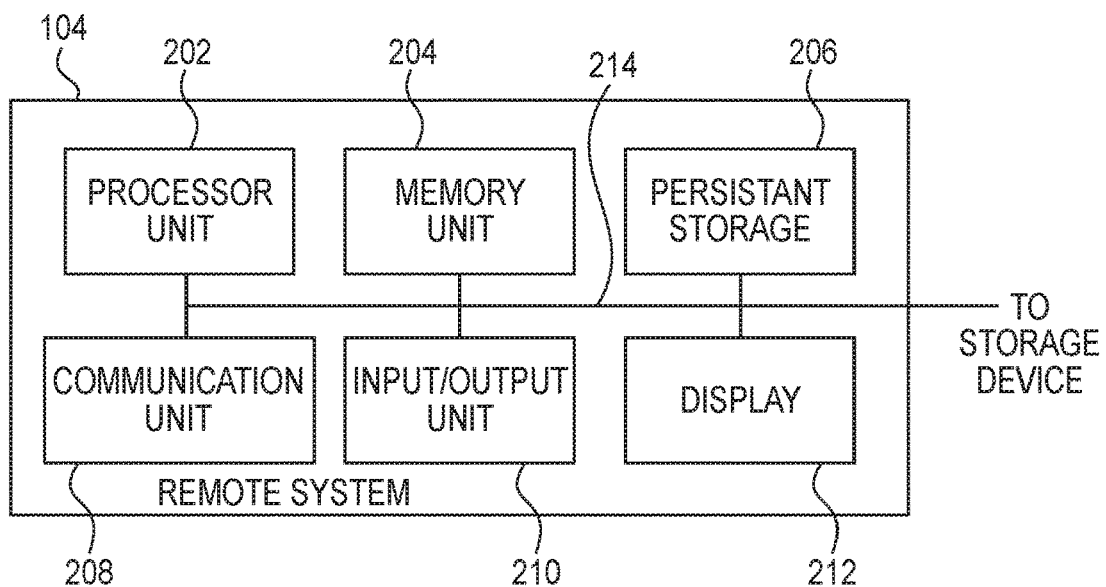
FIG. 2 is a block diagram showing exemplary components of a remote system in accordance with one aspect of the present disclosure.

FIG. 2 is a schematic of a block diagram showing exemplary components of the remote system 104 in accordance with one aspect of the present disclosure. The system 104 may include a processor unit 202, memory unit 204, persistent storage 206, communications unit 208, input/output unit 210, display 212 and system bus 214. Each component may interact with one another through the system bus 214. Fewer or more components may be included within the remote system 104.

Computer programs may be typically stored in the persistent storage 206 until they are ready for execution, at which time the programs are brought into the memory unit 204 so that they can be directly accessed by the processor unit 202. The processor unit 202 may select a part of memory unit 204 to read and/or write by using an address that the processor 202 gives to the memory unit 204 along with a request to read and/or write. The reading and interpretation of an encoded instruction at an address causes the processor 202 to fetch a subsequent instruction, either at a subsequent address or some other address.

The communication unit 208 may be used to provide services locally or remotely. Locally, the remote system 104 may provide capabilities through its input/output unit 210 and display 212. Alternatively, the remote system 104 may be a host service where other devices may access it to process or derive information. The devices may access information from the storage device 106 through the remote system 104.

Figure 3:
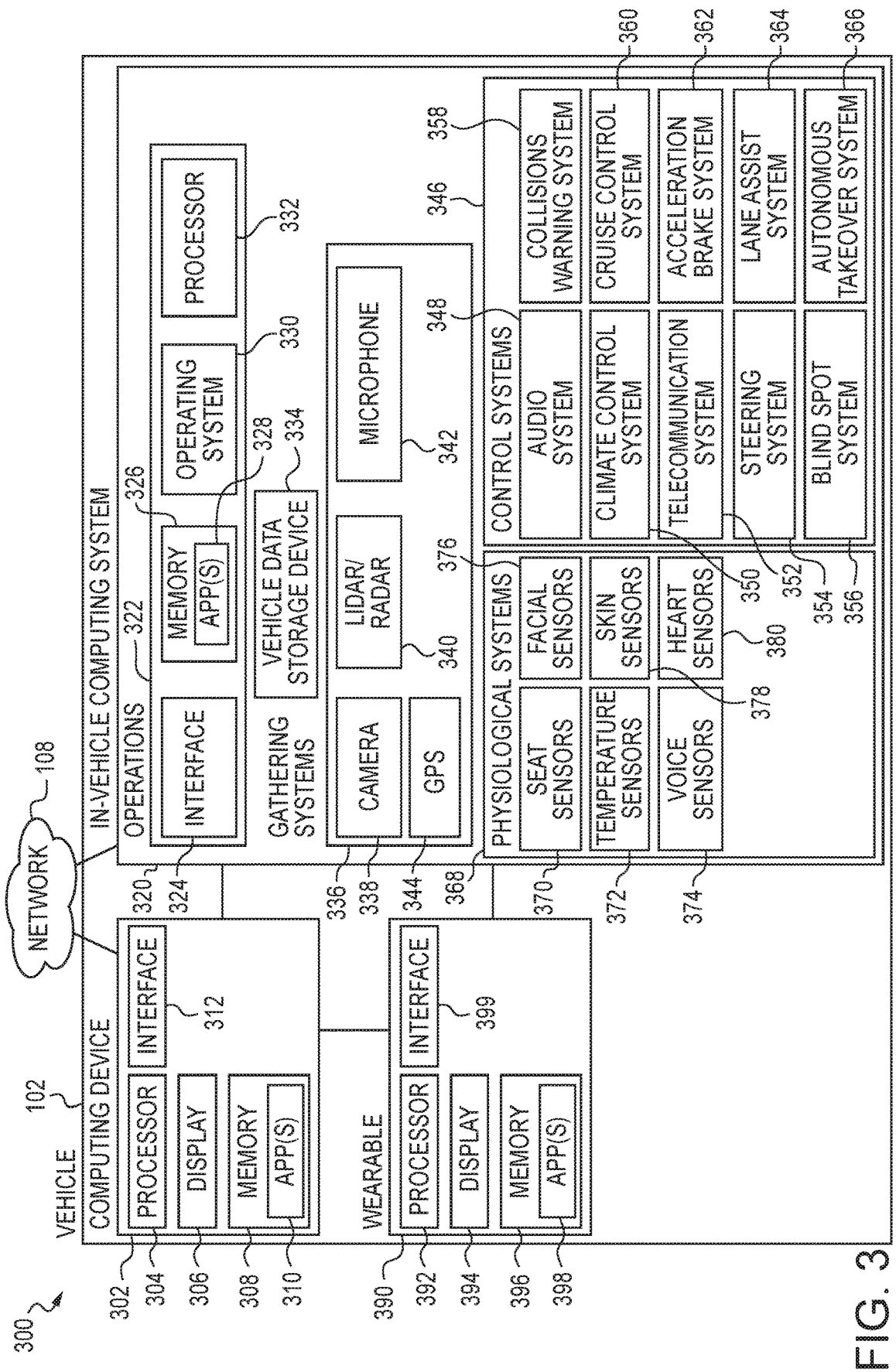
FIG. 3 is a schematic diagram of an illustrative environment for uploading vehicle data through a computing device or in-vehicle computing system in accordance with one aspect of the present disclosure.

Turning to FIG. 3, a schematic diagram of an illustrative environment 300 for uploading vehicle data through a computing device 302 or in-vehicle computing system 320 in accordance with one aspect of the present disclosure is provided. The environment 300 elaborates on those components provided in the earlier discussed environment 100. The vehicle 102 may provide information to the communication network 108 through a computing device 302 or in-vehicle computing system 320 each of which may be within the vehicle 102. In one embodiment, which will be described in more details below, a wearable device 390 may also be provided to detect physiological events from a driver.

While the vehicle data was described as being provided to the remote system 104, both the vehicle data and physiological data may be sent to the remote system 104 through the communication network 108 from the in-vehicle computing system 320. This information may be provided directly through the in-vehicle computing system 320 connected to the communications network 108.

A communication channel may be opened by the in-vehicle computing system 320 with the remote system 104. This channel may be held open continuously and vehicle data and/or physiological data may be sent each time an event is detected. The channel may be closed after the vehicle stops. The driver may close the channel manually within the vehicle 102. Alternatively, the communication channel may be opened each time a physiological event is detected and closed thereafter.

The data may be provided indirectly through the computing device 302 to the communications network 108. Vehicle data and physiological events may be processed on the in-vehicle computing system 320 and the computing device 302 may be used for its connection with the communication network 108. The computing device 302 may be communicatively coupled to the in-vehicle computing system 320 through a wireline, such as a tether, or wirelessly. The computing device 302 may open a communication channel with the network 108 continuously or each time a physiological event is detected.

In one embodiment, the computing device 302 may perform the processing. The computing device 302 may be used to monitor the physiological condition and then pull data from the in-vehicle computing system 320 when an event is detected. Once the information is processed, a communication channel may be opened for this event and closed thereafter or may be left opened.

Components that may be provided within the computing device 302, in-vehicle computing system 320 and wearable device 390 will now be described. The components described for each of the devices and systems are representative illustrations and should not be construed as limiting. Furthermore, multiple computing devices 302 and wearable devices 390 may be provided within the vehicle 102 and is not limited to a single device as shown.

As described earlier, the computing device 302 may be in the vehicle 102 to enable communication between the in-vehicle computing system 320 and the remote system 104. The computing device 302 may be a mobile computing device or any other portable device. In some embodiments, the mobile computing device 302 may be a mobile telephone, laptop, tablet, computing pad, netbook, gaming device and/or portable media player. The computing device 302 may also be less portable devices such as desktop personal computers, kiosks and tabletop devices. Additionally, the computing device 302 may represent a group of processing units or other computing devices.

The computing device 302 and/or the in-vehicle computing system 320 may connect with the remote system 104. The computing device 302 may act as a transport for higher-layer message exchanges between the in-vehicle computing system 320 and the remote system 104. The user computing device 302 and/or in-vehicle computing system 320 may communicate with each other and the remote system 104 using any data or communication transfer protocol. For example, the computing device 302, the in-vehicle computing system 320 and the remote system 104 may exchange information via Bluetooth brand communication, Wi-Fi and/or cellular communication protocols. The computing device 302, the in-vehicle computing system 320 and the remote system 104 may also exchange information via any wired communication protocol, such as in a scenario where the computing device 302 is tethered to the in-vehicle computing system 320 with a cable. The computing device 302 and/or the in-vehicle computing system 320 may have a persistent connection to the remote system 104. In other embodiments, the user computing device 320 and/or the in-vehicle computing system 320 may buffer data to anticipate intermittent loss of connectivity with the communication network 108 (e.g., when moving through an area with poor network coverage) or to save on network bandwidth costs.

The computing device 302 may have at least one processor 304, display 306, memory 308 having a number of applications 310 and interface 312. The processor 304 may include any quantity of processing units and is programmed to execute computer-executable instructions for implementing aspects of the disclosure. The instructions may be performed by the processor 304 or by multiple processors executing within the computing device 302 or performed by a processor external to the user computing device 302.

The computing device 302 may have one or more data stores within memory 308. The memory 308 may include any quantity of media associated with or accessible by the computing device 302. The memory 308 may be internal to the computing device 302, external to the computing device 302 or both. The memory 308 may store, among other data, one or more applications 310. The applications 310, when executed by the processor 304, may operate to perform functionality on the computing device 302. Exemplary applications 310 may include mail application programs, web browsers, calendar application programs, address book application programs, messaging programs, media applications, location-based services, search programs and the like. The applications 310 may communicate with counterpart applications or services such as web services accessible via the communications network 108. For example, the applications 310 may represent downloaded client-side applications that correspond to server-side services executing in the remote system 104.

In one embodiment, the applications 310 may provide a gateway for information to be communicated between the in-vehicle computing system 320 to the remote system 104. Some in-vehicle computing systems 320 with vehicles 102 may not be able to communicate with network services directly as they may lack a transmission control unit (TCU) or other interface. Communications may thus be sent through the computing device 302.

The computing device 102 may perform more functions than simply providing a gateway for the in-vehicle computing system 320. For example, an application 310 on the computing device 102 may determine whether a physiological event has occurred by receiving physiological data from physiological systems 368 within the in-vehicle computing system 320 and/or wearable device 390. Using this information, the application 310 on the computing device 302 may determine whether an event occurred, for example, whether the driver is nervous. The computing system 320 may then retrieve vehicle data from the in-vehicle computing system 320 when an event has occurred. The information may then be provided to the remote system 104.

In one alternative embodiment to that described, the vehicle data may be stored on the computing device 302 instead of the vehicle 102. The computing device 302 may then analyze the physiological information and determine whether an event occurs. The vehicle data stored on the computing device 302 may be sent to the remote system 104 once the event happens.

The computing device 302 may also include a display 306. The display 306 may include any means for displaying and/or receiving data for the user. For example, the display 306 may include a touch screen display for receiving input and providing output. The computing device 302 may be used to establish options and custom configurations. For example, the driver may want to send vehicle data when the wearable device 390 detects an event and not when the physiological system 368 on the in-vehicle computing system 320 detects it. In another example of a customized configuration, the driver may want only facial expressions to be monitored to trigger the vehicle data to be sent to the remote system 104 and only certain facial expressions such as whether the driver is angry.

The interface 312 of the computing device 302 may include a network interface card and/or computer-executable instructions, for example a driver, for operating the network interface card. The interface 312 may allow the computing device 302 to communicate with other systems and devices, including inside and outside the vehicle 102. The interface 312 may be used to communicate with the communications network 108, wearable device 390 or in-vehicle computing system 320. The interface 312 may include wireline or wireless components.

Turning to the in-vehicle computing system 320 of FIG. 3, a number of different systems including operations 322, storage device 334, gathering systems 336, control systems 346 and physiological systems 368 will now be described. Fewer or more systems may be provided within the in-vehicle computing system 320 as well as fewer or more components within those systems. These should not be construed as limiting. The systems were separated into logical partitions, however, this should not be construed as limiting the in-vehicle computing system 320.

The operations 322 of the in-vehicle computing system 320 may include an interface 324, memory 326 which may include applications 328, operating system 330 and processor 332. The interface 324 may be used to communicate with the communications network 108, wearable device 390 or computing device 302. The interface 324 may include a network interface card and/or computer-executable instructions for operating the network interface card. The in-vehicle computing system 320 may communicate with other systems and devices using any data or communication transfer protocol through the interface 324 provided within the operations 322.

The in-vehicle computing system 320 may have one or more data stores within the memory 326. The memory 326 may include any quantity of media associated with or accessible by the in-vehicle computing system 320. The memory 326 may store, among other data, one or more applications 328. The applications 328, when executed by the processor 332, may operate to perform functionality on the in-vehicle computing system 320. Exemplary applications 328 may include mail application programs, web browsers, calendar application programs, address book application programs, messaging programs, media applications, location-based services, search programs and the like. The applications 328 may communicate with counterpart applications or services such as web services accessible via the communications network 108 through the interface 324. For example, the applications 328 may represent downloaded client-side applications that correspond to server-side services executing in the remote system 104, computing device 302 or wearable device 390.

Multiple applications 328 may run processes for obtaining vehicle data as well as detecting physiological events. For example, an application 328 within the operations 322 may be used solely to determine whether the driver is happy or nervous and another application 328 may be used for pulling steering information. Applications 328 may interact with one another to determine whether a physiological event has occurred. For example, seat information may be combined with facial expressions to conclude that a driver is hot.

The applications 328 may be used to retrieve vehicle data from the gathering systems 336 and control systems 346. The data may be stored into the vehicle data storage device 334, which will be described in further details below. Other applications 328 within the memory 326 may include processes for running the control systems 346. For example, the audio system 348 or climate control 350 may run applications 328 that help them operate. An application 328 for the climate control 350 may have special software for syncing multiple heating, ventilating and air conditioning (HVAC) units. The processes may sync all the units when a button is pressed.

In another example, the applications 328 may be used to control the blind spot system 356. The blind spot control system 356 may take in a number of different inputs and then provide a warning to the driver if a vehicle or other object is within a difficult area to see. The system 356 may provide audio or visual warnings to the driver. Other control systems 346 will be described below.

The operations 322 of the in-vehicle computing system 320 may be programmed to execute computer-executable instructions for implementing aspects of the disclosure. The instructions may be performed by the processor 332 or by multiple processors executing within the in-vehicle computing system 320 or performed by a processor external to the user in-vehicle computing system 320.

The memory 326 may include both volatile memory (e.g., RAM) and non-volatile memory (e.g., ROM, Flash Memory or the like). The non-volatile portion of the memory 326 may be used to store persistent information which should not be lost when in-vehicle computing system 320 is powered down. The operations 322 of the in-vehicle computing system 320 may include an operating system (OS) 330, such as the iOS operating system available from Apple Inc., the Android® operating system available from Google Inc., the Windows operating system available from Microsoft Corporation or any other similar OS. The OS may reside in the memory 326 or separately therefrom and be executed on the processor 332.

The gathering systems 336 of the in-vehicle computing system 320 shown in FIG. 3, may be used to collect environmental data. The systems 336 may be placed on a non-autonomous, semi-autonomous or autonomous vehicle 102. The systems 336 may use pre-existing structures on the vehicle 102 or structures that may be added to the vehicle 102 for the purpose of gathering the vehicle data. The gathering systems 336 may also be used to support the control systems 346, for example, the lane assist system 364 within the control systems 346 may receive images from the cameras 338 in the gathering systems 336. The gathering systems 336 may include, but are not limited to, optical, audio and/or positioning sensors. These may include cameras 338, lidar/radar 340, microphones 342 and/or GPS 344.

In one embodiment, cameras 338 may be used to retrieve vehicle data. Images or video may be captured through the cameras 338. A light source may be provided with the cameras 338 which may provide near-instantaneous flash or may provide a continuous illumination. Images or video may be saved in a variety of formats. Images from the cameras 338 may be processed automatically by adjusting for focus, for example, objects may be identified within the image and the objects may be focused on. Automatic zoom features may also be included on the cameras 338. These features may be software or hardware based or a combination of both. Multiple cameras 338 may be used on the exterior and/or interior, some of which may vary in view angles. Images or video may be used to modify automated driving functionalities by determining which objects within a scene the vehicle 102 should be concerned about.

Lidar and/or radar 340 may be included into the gathering systems 336. Lidar may include a sensor configured to sense objects in the environment in which the vehicle 102 is located using lasers. Depending upon the embodiment, the laser rangefinder may include one or more laser sources, a laser scanner and one or more detectors, among other system components. The laser rangefinder may be configured to operate in a coherent or an incoherent detection mode. The radar may represent a system that utilizes radio signals to sense objects within the local environment of the vehicle 102. In some embodiments, in addition to sensing the objects, the radar may additionally be configured to sense the speed and/or heading of the objects. Similar to the cameras 338 above, vehicle data from the lidar and/or radar 340 may be used to understand which objects are around the vehicle 102 to modify automated driving functionalities.

The gathering systems 336 may also include the microphone 342. The microphone 342 may be configured to capture sound from the environment surrounding the vehicle 102 or within the vehicle 102. In some cases, multiple microphones 342 can be arranged as a microphone array or possibly as multiple microphone arrays. The microphone 342 may capture vehicle data within the vehicle 102 or outside the vehicle 102. Vehicle data captured from the microphone 342, for example, may be used to modify automated driving functionalities by detect emergency vehicles from an external microphone 342 and then adjust those functions based on the emergency vehicle detection.

The GPS 344 may be any sensor configured to estimate a geographic location of the vehicle 102. The GPS 344, which may be part of the gathering systems 336, may include a transceiver operable to provide information regarding the position of the vehicle 102 with respect to the Earth. Differential global positioning system (DGPS) information may also be captured, which may provide a more enhanced coordinate system and exact location information. Adjusting automated driving functionalities may be based on the GPS information as the vehicle 102 may be directed to another route using this information.

Multiple systems 336, described above, may be used in the vehicle 102 to gather combinations of vehicle data. The gathered vehicle data from some or all of the systems 336 may be selected depending on the physiological event detected. The vehicle data may be stored in the vehicle data storage device 334, which will be shown in FIG. 4.

In addition to the vehicle data from the gathering systems 336 and continuing with FIG. 3, the data may come from the control systems 346. Vehicle data that comes from the control systems 346 may generally come from, but is not limited to, an audio system 348, climate control system 350, telecommunication system 352, steering system 354, blind spot system 356, collision warning system 358, cruise control system 360, acceleration/brake system 362, lane assist system 364 or autonomous takeover system 366. Fewer or more components within the control systems 346 may be removed or added. These systems are for illustrative purposes and should not be construed as limiting.

Vehicle data may be retrieved from the audio system 348. The audio system 348 may be provided through a display unit having a touch screen or the like. Vehicle data through the audio system 348 may include, but is not limited to, stations on which a user has selected, genre of music or programming or frequency of switching stations. In one example, frequency of switching stations may be used by the remote system 104 to modify how often the driver is expected to take over manual controls as the driver may be more focused on the audio system 348 than the driving of the vehicle 102. Automated functionality may be modified or altered based on the incoming vehicle data when a physiological event has been detected.

Vehicle data from the climate control system 350 may be provided or stored within the vehicle data storage device 334. The climate control system 350 may also operate on the display unit having the touch screen or be manually adjusted through knobs or buttons. Vehicle data from the climate control system 350 may include, but is not limited to, temperature settings, frequency of changes to the temperature or fan levels. This data may be collected to modify automated driving functionalities by, for example, presetting the climate within the vehicle 102 to reduce workload on the driver.

The telecommunication system 352 may be monitored for vehicle data that includes, but is not limited to incoming and outgoing calls, text and multimedia messaging service data usage, for example. This vehicle data may be used for modifying automated driving functionalities. For example, the higher the amount of data, the more workload the driver may have and modifying functions on the vehicle may be implemented to reduce the workload.

The control systems 346 may also monitor the steering system 354 for vehicle data. This vehicle data may include, but is not limited to, steering angles at which the vehicle 102 is directed at or how fast the angles were turned to. Automated driving functions may be modified using this data by taking into account how the driver is making a left turn at an intersection, for example.

The blind spot system 356 of the control systems 356 may be used to detect other vehicles through object sensors. Vehicle data associated with the blind spot system 356 may include, but is not limited to, areas surrounding the vehicle 102 that are hardest to see by the driver or where vehicles are most likely to be in a blind spot. The blind spot system 356 may use the cameras 338 or lidar and/or radar 340 described above. This vehicle data may be collected or used to modify automated driving functionalities, for example, reducing the amount of blind spot warnings by analyzing an area around the vehicle 102 where they are most likely to occur.

The collision warning system 358 of the control systems 356 may refer to whether the driver's vehicle 102 may impact an object in front or from behind. For example, warnings may be provided when the vehicle 102 backs out of a parking space and another vehicle is approaching. Automated driving functionalizes may use this data to determine dangerous situations and adjust those functions when parking or exiting a space, for example. In another example, the vehicle data received from the collision warning system 358 may be used to adjust functions by fine tuning lane changes when an object is detected in front of the vehicle 102.

The control systems 356 may also include a cruise control system 360. The vehicle data pulled from the cruise control system 360 may include, but is not limited to, speed set, how often the speed is increased or reduced for ACC system or the distance between the vehicle 102 and the preceding vehicle. This vehicle data may be used, for example, to adjust the distance between the vehicle in front depending on physiological events detected.

The acceleration and/or brake system 362 may also provide vehicle data for which may be sent to the remote system 104 to adjust automated driving functionalities. This data may include, but is not limited to, how often the driver presses on the accelerator and/or brake or the intensity at which they are pressed. Modified automated driving functionalities using this vehicle data may include changing autonomous driving styles, for example.

The lane assist system 364 of the control systems 346 may be used to keep a vehicle within a lane. Vehicle data may be warnings when the vehicle 102 deviates outside of the driver's lane. This vehicle data may be used to modify automated driving functionalities by adjusting the auto steering to reducing these warnings, for example.

Vehicle data from the autonomous takeover system 366 may be captured and/or monitored. Semi-autonomous or autonomous vehicle take over systems 366 may include controls that are provided to a user if the vehicle 102 does not understand how to handle the situation. For example, if the vehicle 102 is entering into a urban area and is not programmed for the urban area, control may be given back to the driver before entering into the urban area. Also, if the processor 332 is getting overwhelmed with information, and a processing slowdown occurs, the driver may be asked to use the steering wheel by the autonomous takeover system 366. In another example, the autonomous takeover system 366 may allow the driver to perform other tasks while the vehicle 102 is taken over by the in-vehicle computing system 320. These controls may include stopping, going, or yielding at an intersection or stop sign, for example. This vehicle data received from the autonomous takeover system 366 may include, but is not limited to, how often the driver takes over control from the autonomous vehicle or how long it takes to take over the vehicle. The automated driving functionalities may be adjusted or modified by providing warnings using this vehicle data.

As described above, the gathering systems 336 and control systems 346 were used to retrieve or pull vehicle data to modify automated driving functions. Other components within the systems 336 and 346 may be used to obtain vehicle data. Vehicle data from both systems 336 and 346 may result in a large amount of data being sent to the remote server 104. Consequently, a trigger may be used to reduce the amount of vehicle data being sent, which will now be described in detail below.

Continuing with FIG. 3, the physiological system 368 of the in-vehicle computing system 320 may provide the trigger for which vehicle data may be sent to the remote server 104. The physiological system 368 may include, but is not limited to, seat sensors 370, temperature sensors 372, voice sensors 374, facial sensors 376, skin sensors 378 or heart sensors 380. Fewer or more components may be used for the physiological system 368. Some of these systems 368 may require complex algorithms or data that may be run as an application within memory 326 which will become apparent from the discussion provided below. Furthermore, while the physiological system 368 is shown within the in-vehicle computing system 320, the physiological systems 368 may be located on the computing device 302, wearable device 390 or other system.

In one physiological system 368, seat sensors 370 may be used to trigger sending vehicle data to the remote system 104. The seat sensors 370 may be used to detect moisture, for example. When a driver sweats, a physiological event may be detected. The seat sensors 370 may also be used to determine the temperature or heart rate of a driver. In one embodiment, the seat sensors 370 may be used to determine nervous movements or gestures by the driver. A seat sensor 370 may be placed in the driver's leg area to detect muscle movements to derive a physiological event. The seat sensor 370 may be a simple motion detection sensor or may be more complex such as a larger pad sensor that monitors the muscle movements in the driver's legs. While some movements are expected, nervous movements may be characterized in sharp and quick movements.

Figure 11:
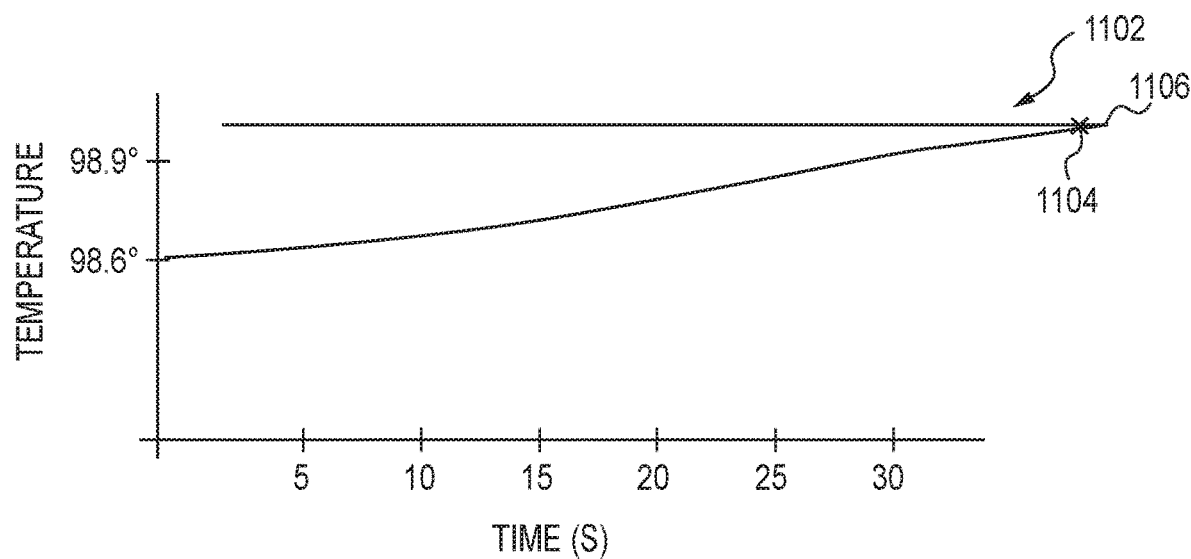
FIG. 11 is an illustrative chart showing an increase in temperature of the driver depicting a physiological event in accordance with one aspect of the present disclosure.

Temperature sensors 372 may be used to trigger the sending of vehicle data to the remote system 104. Temperatures may indicate that the driver is angry, nervous, etc. For example, when a driver's temperature increases, albeit slightly, the driver may be angry or upset. This may result from their driving situation, for example, a lot of traffic. In another example, a decrease in a driver's temperature may indicate that the driver is tired or drowsy. The decrease in temperature may also indicate that they are not alert or too relaxed for driving. Cameras, or other sensors, may be used to detect the temperature of the driver. These cameras may be focused on a driver's face, or other portion of the body where the temperature of the driver may be determined. Other types of sensors may be used to detect the temperature of the driver including sensors on a wearable device 390, which will be described below. FIG. 11, below, will provide more description on how a physiological event is detected by a driver's temperature.

Figure 12:
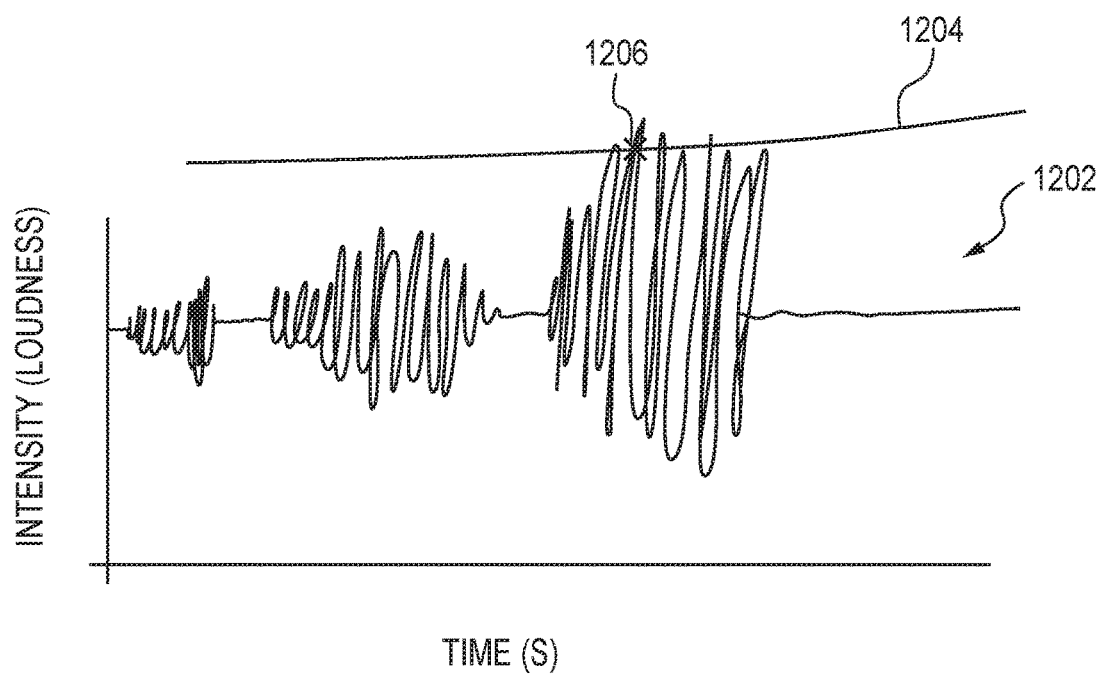
FIG. 12 is an illustrative chart showing a voice inflection depicting a physiological event in accordance with one aspect of the present disclosure.

In one embodiment, voice sensors 374 may be used to detect a physiological event. Voice inflections may be monitored to trigger sending vehicle data to the remote system 104. An in-vehicle microphone may be used to detect the voice inflections. In one example, when the driver is screaming, vehicle data may be sent such as images or video captured from the surrounding environment along with vehicle data from the microphone. FIG. 12 will provide more description on how a physiological event is detected by a driver's voice inflections. Typically, the physiological event occurs after a certain threshold is met. In one embodiment, background noise may be filtered out from the voice patterns detected by the microphone. Further, specific voice patterns from the driver may be separated from passengers within the vehicle 102 such that the driver's voice may be specifically analyzed. Voice patterns of different users may be differentiated, for example, a female voice pattern is different from a male voice pattern.

Figure 13:
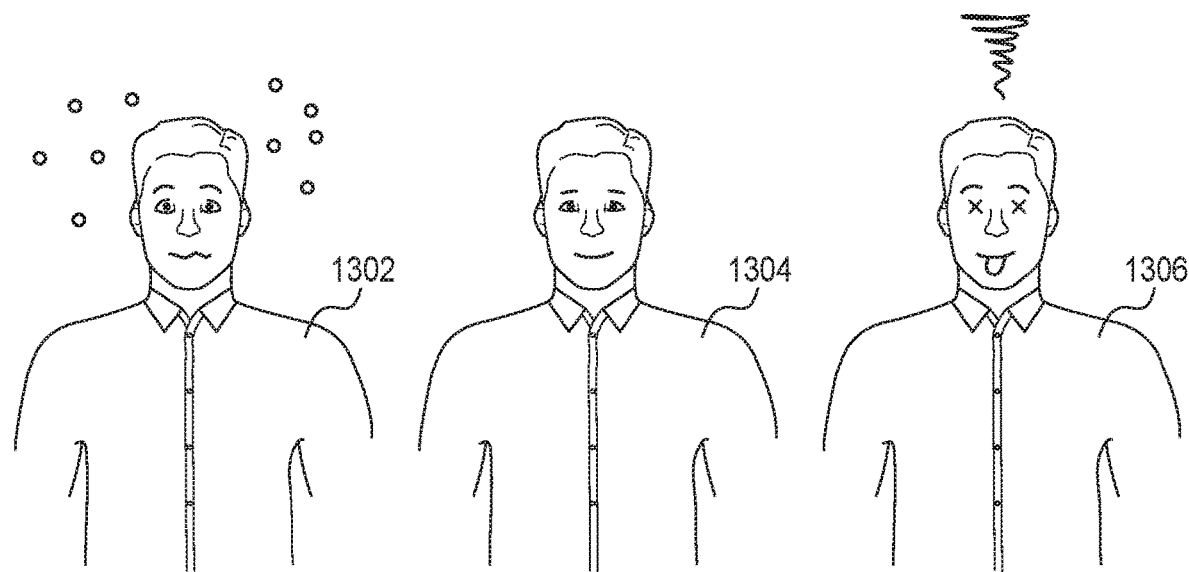
FIG. 13 is an illustrative image of exemplary facial expressions to show different physiological states of a driver in accordance with one aspect of the present disclosure.

Facial sensors 376 may be part of the physiological system 368 to determine whether vehicle data should be provided to the remote system 104. In one example, facial determinations may be analyzed by taking a number of points on a driver's face. Applications 328 may be used for this processing. Training images may be used in a machine based learning algorithm. Certain captured facial expressions from the facial sensors 376 may cause the trigger to be made. In one example, determinations regarding a driver's face may be made based on the driver's mouth, eyes, skin, eyebrows or a combination thereof. FIG. 13 will provide more description on how a physiological event is detected by the facial sensors 376.

Skin sensors 378 may be used to provide the trigger. Skin sensors 378 may detect a number of different variables that trigger a physiological event. The sensors 378 may determine a perspiration level, temperature or blood flow, for example. Perspiration flow may be determined by a camera or other types of device. These sensors 378 may be placed in a wearable 390. Perspiration may also be determined within the seat of the driver.

Figure 10A:
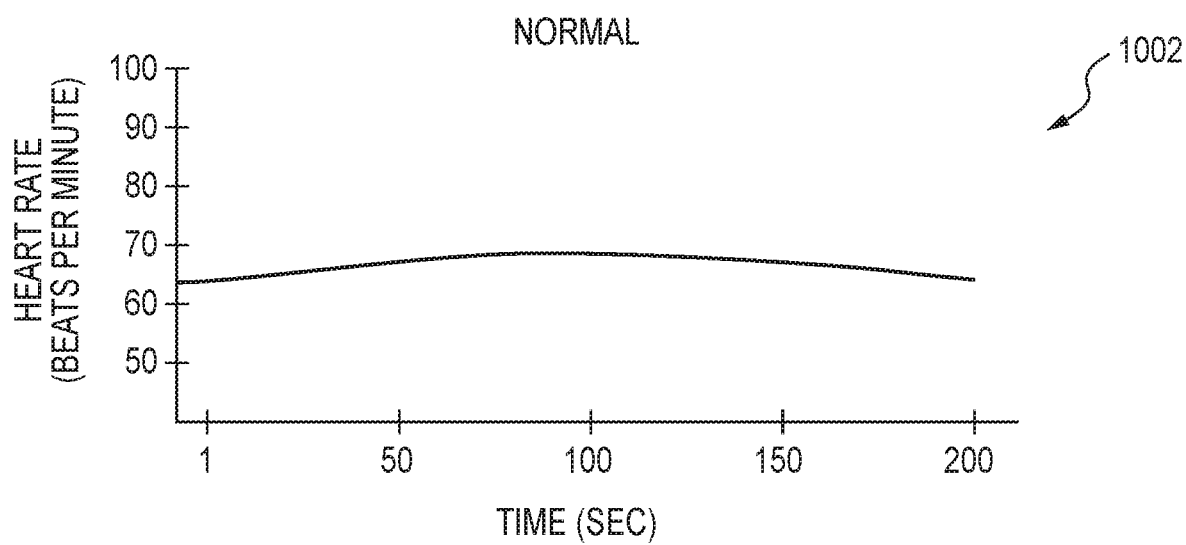
FIG. 10A is an illustrative chart for depicting a normal physiological state using the driver's heart rate in accordance with one aspect of the present disclosure.
Figure 10B:
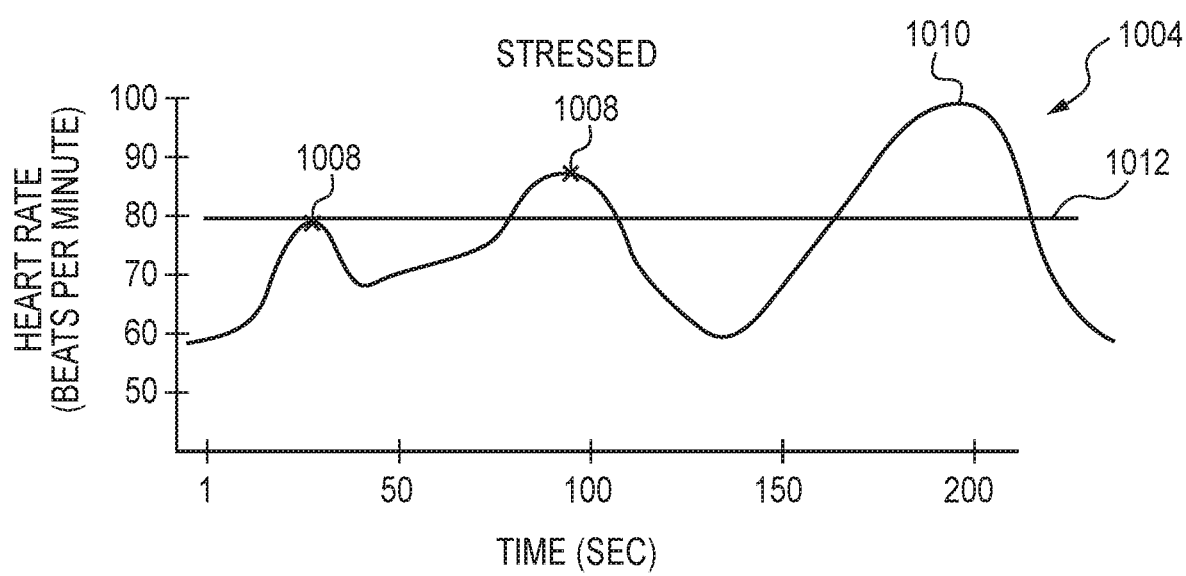
FIG. 10B is an illustrative chart for depicting a stressed physiological state using the driver's heart rate in accordance with one aspect of the present disclosure.

Heart sensors 380 may be used to trigger uploading of vehicle data to the remote system 104. The sensors 380 may be focused on the driver and within certain locations of the driver's body. Heart monitors may be used that may be connected to the driver through a wearable device 390 or in some embodiments, a camera may be able to detect the heart rate of a driver through their clothes. In one example, the wearable device 390, on an interior portion of a watch, may be used to detect the heart rate by taking the driver's pulse. The driver's pulse may be monitored and counted for heart beats. In another example, a camera may be pointed directly at the driver's chest to monitor the driver's heart. These cameras may detect slight variations of the driver's cloths above their chest to monitor the driver's heartbeat. FIGS. 10A and 10B will provide more description on how a physiological event is detected by the heart sensors 380

Fewer or more physiological systems 368 may be used to detect a physiological event that may cause sending vehicle data to the remote system 104. Combinations of those systems 368 may be used. For example, the temperature of the driver may be determined through seat sensors 370 and confirmed by skin sensors 376. In one embodiment, combinations of different physiological events may be used to send the vehicle data, for example, an increase in heart rate in conjunction with a nervous facial expression may be used as the trigger to send vehicle data to the remote system 104.

The wearable device 390, as shown in FIG. 3, may also be used to provide a trigger to send vehicle data. The wearable device 390 may detect a perspiration level, temperature or blood flow of the driver, as described above for example. The wearable device 390 may include, but is not limited to, glasses, wrist watch, necklace, bracelet or the like. The wearable device 390 may monitor temperature, pulse, oxygen level in the blood, etc. of the driver. The wearable device 390 may have at least one processor 392, display 394, memory 396 having a number of applications 398 and interface 399.

The processor 392 may include any quantity of processing units and is programmed to execute computer-executable instructions for implementing aspects of the disclosure. The instructions may be performed by the processor 392 or by multiple processors executing within the wearable device 390 or performed by a processor external to the wearable device 390.

The wearable device 390 may have one or more data stores within memory 396. The memory 396 may include any quantity of media associated with or accessible by the wearable device 390. The memory 396 may be internal to the wearable device 390, external to the wearable device 390 or both. The memory 396 may store, among other data, one or more applications 398. The applications 398, when executed by the processor 392, may operate to perform functionality on the wearable device 390. Exemplary applications 396 may include mail application programs, web browsers, calendar application programs, address book application programs, messaging programs, media applications, location-based services, search programs and the like. The applications 396 may communicate with counterpart applications or services such as web services accessible via the communications network 108. Some applications 398 may be used to extract physiological events from the driver. This information may be communicated to the computing device 302 or in-vehicle computing system 320. In one embodiment, the wearable device 390 may directly communicate with the remote system 108 or the computing device 302 as described above.

The interface 399 of the wearable device 390 may include a network interface card and/or computer-executable instructions, for example a driver, for operating the network interface card. The interface 399 may allow the wearable device 390 to communicate with other systems and devices, including inside and outside the vehicle 102. The interface 399 may be used to communicate with the communications network 108, computing device 302 or in-vehicle computing system 320. The interface 399 may include wireline or wireless components.

Figure 4:
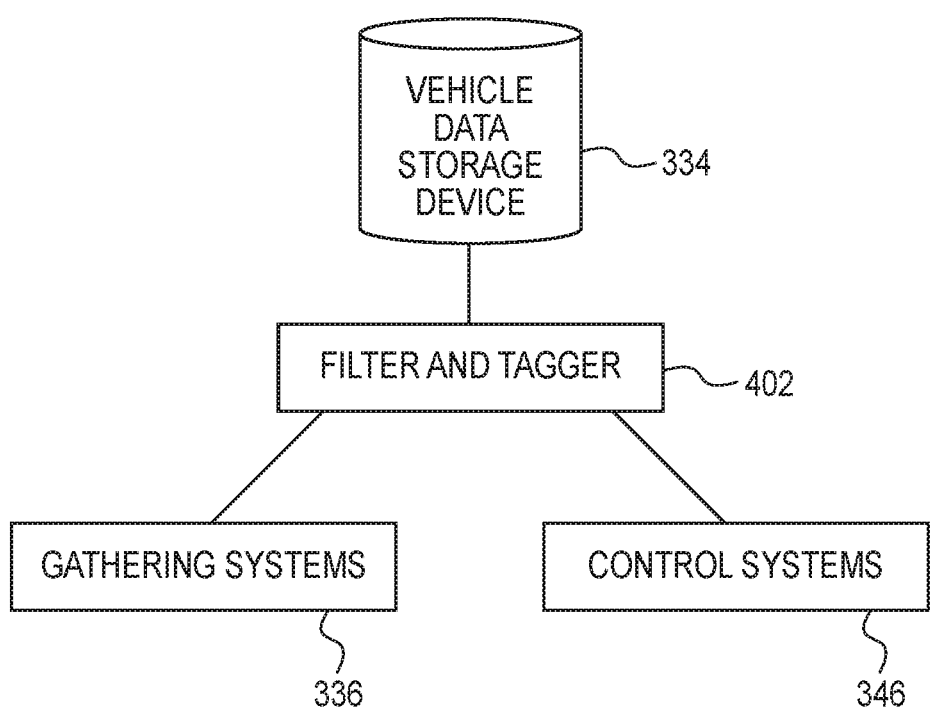
FIG. 4 is a schematic diagram of a typical vehicle storage device receiving data from a number of sources in accordance with one aspect of the present disclosure.

As described above, gathering systems 336 and control systems 346 may provide vehicle data. The vehicle data may be stored within the vehicle data storage device 334. FIG. 4 is a typical vehicle storage device 334 receiving data from a number of sources in accordance with one aspect of the present disclosure. Vehicle data may be differentiated from physiological data as vehicle data is related to the vehicle and physiological data is associated with the driver.

The vehicle data may be stored in the vehicle data storage device 334. When stored, vehicle data from the gathering systems 336 and control systems 346 may be provided to the filter and tagger 402. The filter may be used to remove vehicle data having errors. The filter may also be used to select vehicle data for storage based on a specific physiological event. For example, vehicle data from the cameras 338, lidar and/or radar 340, GPS 344, microphone 342 telecommunication system 352, steering system 354, blind spot system 356 and collision warning system 358 may be stored based on a stressed determination as indicated by a driver's heart rate. The vehicle data may be stored and immediately sent to the remote system 104 or sent in the future. Further examples of selecting vehicle data based on physiological events will be described in FIG. 16.

In addition, the filter and tagger 402 may time stamp the vehicle data. Time stamping the incoming vehicle data may allow synchronization of the data. For example, multiple components within the gathering systems 336 and control systems 346 are continuously providing data. Each of these components may not be synched with one another especially across the systems 336 and 346. Time stamps may allow for the vehicle data to be put together to show an accurate environmental picture.

Tagging the vehicle data through the time stamps may be used when a physiological event is detected. The time at which the physiological event is determined may be then be used to access the vehicle data storage device 334 and vehicle data captured around the time of the event. While sending specific vehicle data related to the detected physiological event was shown above, all vehicle data around the time of the event may also be sent. This vehicle data may be processed on the remote system 104.

In one embodiment, the filter and tagger 402 may also tag vehicle data for specific drivers. Vehicle data may be captured based on the driver as often times vehicles 102 may be shared among a number of different users. Automated driving functionalities may be adjusted based on the driver when the vehicle data is provided to the remote system 104. For example, one driver may be more aggressive than another. When automated driving functionalities are adjusted for an autonomous vehicle, the specific driver may be determined and those settings or parameters adjusted accordingly.

Figure 5:
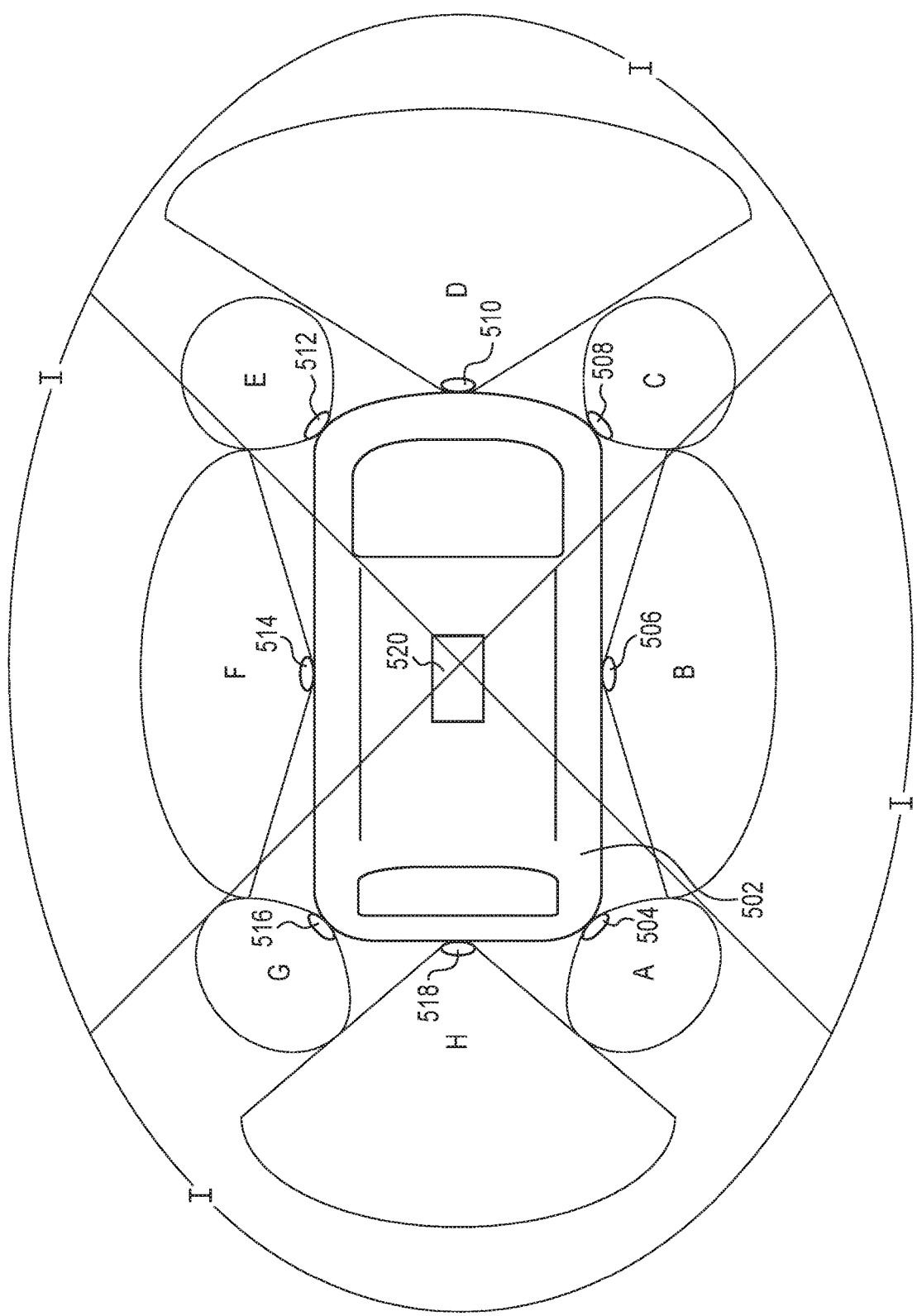
FIG. 5 is a schematic diagram of an exemplary vehicle retrieving data from a number of different sensors in accordance with one aspect of the present disclosure.

As described above, vehicle data may be gathered from the gathering systems 336 and control systems 346. FIG. 5 is a schematic diagram of an exemplary vehicle 502 retrieving data from a number of different sensors 504, 506, 508, 510, 512, 514, 516, 518 and/or 520 in accordance with one aspect of the present disclosure. For illustrative purposes, these sensors 504, 506, 508, 510, 512, 514, 516, 518 and/or 520 may be part of the gathering systems 336 which may include the cameras 338, lidar/radar 340 and/or microphones 342 described above. Other types of sensors may be used and are not limited to the cameras 338, lidar/radar 340 and/or microphones 342.

This vehicle data may be provided and analyzed by the remote system 104 for modifying automated driving functions. For example, and as illustrated above, sensors 508, 510 and/or 512 may be used to detect lane lines. This information may be used to modify functions by detecting lines which may not be normal and then modifying automated functionalities by switching to another system for determining a vehicle's position within a lane. In the example above, a DGPS may be used to determine which lane the driver is in.

Each of the sensors 504, 506, 508, 510, 512, 514, 516, 518 and/or 520 may be positioned at different locations on the exterior of the vehicle 502 and be positioned at different angles such that a full environmental picture may be captured. In one embodiment, different configurations of the sensors 504, 506, 508, 510, 512, 514, 516, 518 and/or 520 may be switched on and/or off. For example, sensors 508, 510 and 512 may be turned on while sensors 504, 506, 514, 516, 518 and 520 are turned off such that vehicle data from the front of the vehicle 502 is captured. In another example, sensors 512, 514 and 516 are turned on and sensors 504, 506, 508, 510, 518 and 520 are switched off to capture vehicle data on the left side of the vehicle 502.

In one embodiment, some of the sensors 504, 506, 508, 510, 512, 514, 516, 518 and/or 520 may work together to capture the environmental picture. For example, sensors 508 and 512 may be activated or deactivated at the same time to capture front side views of the vehicle 502. Sensors 504, 506 and 508 may also be activated at the same time to capture a right side view of the vehicle 502. A number of possible configurations of activating and deactivating sets of sensors 504, 506, 508, 510, 512, 514, 516, 518 and/or 520 may be used by the vehicle 502.

Figure 6:
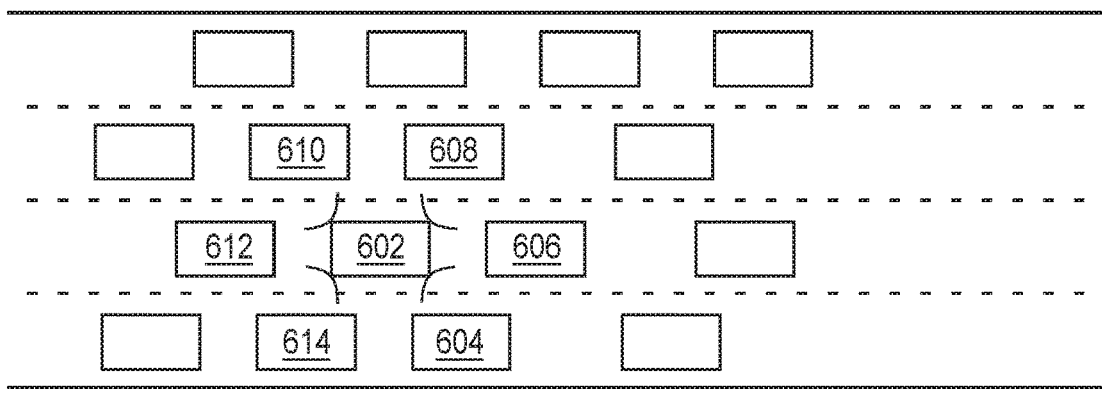
FIG. 6 is a schematic diagram of an exemplary vehicle stuck in traffic retrieving data from a number of different gathering and control systems in accordance with one aspect of the present disclosure.
Figure 7:
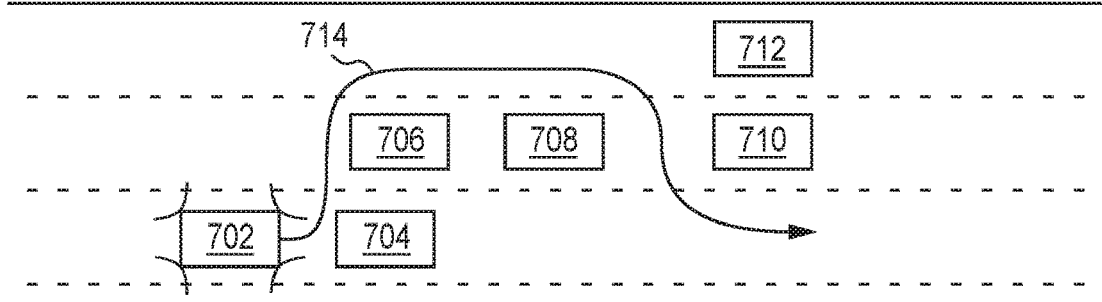
FIG. 7 is a schematic diagram of an exemplary vehicle showing an aggressive driver retrieving data from a number of different gathering systems and control systems in accordance with one aspect of the present disclosure.
Figure 8:
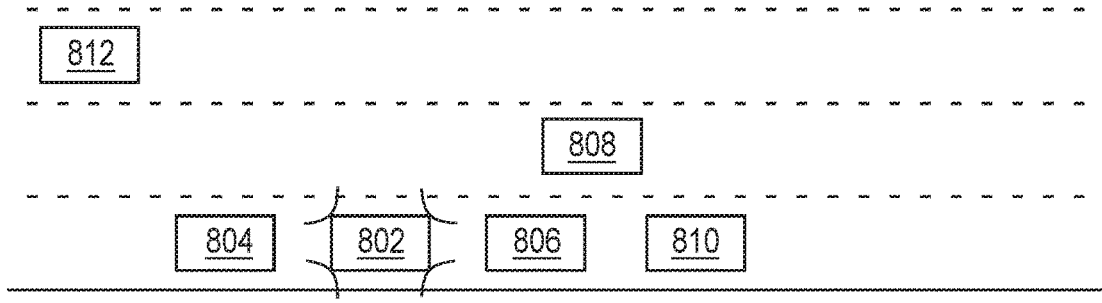
FIG. 8 is a schematic diagram of an exemplary vehicle yielding to an emergency vehicle that retrieves data from a number of different gathering systems and control systems in accordance with one aspect of the present disclosure.

FIGS. 6 through 8 will provide exemplary scenarios where these sensors 504, 506, 508, 510, 512, 514, 516, 518 and/or 520 may be used to determine environmental and situational vehicle data. Further, specifics about modifying automated driving functionalities will be provided in relation to these sensors and physiological events that may occur to send the vehicle data to the remote system 104.

Sensor 504 may be used to cover Area A which is directed towards the back right side of the vehicle 502. Sensor 506 may be used to cover Area B which is directed towards the right side of the vehicle 502. Sensor 508 may be used to cover Area C which is directed towards the front right side of the vehicle 502. Sensor 510 may be used to cover Area D which is directed towards the front of the vehicle 502.

Sensor 512 may be used to cover Area E which is directed towards the front left side of the vehicle 502. Sensor 514 may be used to cover Area F which is directed towards the left side of the vehicle 502. Sensor 516 may be used to cover Area G which is directed towards the back left side of the vehicle 502. Sensor 518 may be used to cover Area H which is directed towards the back side of the vehicle 502.

Sensor 520 may be used to cover Area I which may encompass three hundred and sixty degrees around the vehicle 502. The sensor 520 may be cameras 338, lidar/radar 340 or microphones 342. The sensor 520 may be placed on heightened position on the vehicle 502 such that any environmental pictures taken may not be impeded by the vehicle body or other structure on the vehicle 502.

The sensors 504, 506, 508, 510, 512, 514, 516, 518 and/or 520 may provide one environmental picture captured by the gathering systems 336. Multiple variations may exist including using other components found in both the gathering systems 336 and control systems 346. Based on the detection of a physiological event, vehicle data from the sensors 504, 506, 508, 510, 512, 514, 516, 518 and/or 520 may be provided.

To illustrate physiological events with the use of those sensors 504, 506, 508, 510, 512, 514, 516, 518 and/or 520 presented above in FIG. 5, a number of scenarios will now be described. FIG. 6 is a schematic diagram of an exemplary vehicle 602 stuck in traffic retrieving data from a number of different gathering systems 336 and control systems 346 in accordance with one aspect of the present disclosure. The vehicle 602 may capture vehicle data using the gathering systems 336 which may include optical, audio and/or positional sensors. These may include cameras 338, lidar/radar 340, microphones 342 and/or GPS 344.

In one example, distances between the vehicle 602 and the surrounding vehicles 604, 606, 608, 610, 612 and 614 may be kept track of using those gathering systems 336 including the sensors 504, 506, 508, 510, 512, 514, 516, 518 and/or 520 shown above. Sensor 504, which is directed towards the back right side of the vehicle 502, may detect vehicles 612 and/or 614. Sensor 506, which is directed towards the right side of the vehicle 502, may be used to detect vehicles 614 and/or 604. Sensor 508, which is directed towards the front right side of the vehicle 502, may be used to detect vehicles 604 and/or 606. Sensor 510, which is directed towards the front of the vehicle 502, may be used to detect vehicles 606 and/or 608.

Sensor 512, which is directed towards the front left side of the vehicle 502, may be used to detect vehicles 606 and/or 608. Sensor 514, which is directed towards the lefts side of the vehicle 502, may be used to detect vehicles 608 and/or 610. Sensor 516, which is directed towards the back left side of the vehicle 502, may be used to detect vehicles 610 and/or 612. Sensor 518, which is directed towards the back side of the vehicle 502, may be used to detect vehicles 610, 612 and/or 614. Sensor 520, which may encompass three hundred and sixty degrees around the vehicle 502, may be used to detect vehicles 604, 606, 608, 610, 612 and/or 614.

Images, video, readings, and/or other vehicle data captured by the sensors 504, 506, 508, 510, 512, 514, 516, 518 and/or 520 of the vehicles 604, 606, 608, 610, 612 and/or 614 may be then provided to the remote system 104, when a physiological event is detected. Other vehicles may be kept tracked of outside the surrounding areas as well.

In one embodiment, speeds of the vehicles 604, 606, 608, 610, 612 and/or 614 may also be retrieved or stored as vehicle data. For example, images captured from the sensors 504, 506, 508, 510, 512, 514, 516, 518 and/or 520 may be processed to determine the distance between the vehicle 602 and the other vehicles 604, 606, 608, 610, 612 and/or 614. A time period may be captured, and with the change in distance, the speed of the surrounding vehicles 604, 606, 608, 610, 612 and/or 614 may be determined. Vehicle data regarding the speeds of the other vehicles 604, 606, 608, 610, 612 and/or 614 may be sent to the remote system 104, along with the other described vehicle data, to the remote system when a triggering physiological event has been made. The speed of the vehicle 602 capturing the vehicle data may be taken into account when the images are processed. For example, if the vehicle 602 is moving, a difference between the speed of the vehicle 602 and the other vehicles 604, 606, 608, 610, 612 and/or 614 may be used to determine the speed of the other vehicles 604, 606, 608, 610, 612 and/or 614.

Within the surroundings of the vehicle 602, vehicle data may also come from the control systems 346 which may include the audio system 348, climate control 350, telecommunication system 352, steering system 354, blind spot system 356, collision warning system 358, cruise control system 360, acceleration/brake system 362, lane assist system 364 or autonomous takeover system 366. Vehicle data that may be important when modifying automated driving functionalities may include how often the accelerator or brake pedal is being pressed, times collision warnings goes off, etc. The vehicle data from the control systems 346 may be combined with the gathering systems 336 and when a physiological event occurs, the vehicle data is provided to the remote system 104.

In the stuck in traffic scenario provided in FIG. 6, the physiological system 368 may trigger the vehicle data to be sent to the remote system 104 after an upset facial detection is made, for example. Another trigger may include an increase in heart rate or voice inflection showing that the driver is angry, which will be described in FIGS. 10 and 12. The vehicle data including the environment created by the surrounding vehicles 604, 606, 608, 610, 612 and/or 614 through captured images may be provided. Further, braking and acceleration vehicle data may be provided to the remote system 104. One example of modified automated driving functions may include changing music within the vehicle 602 after receiving the vehicle data. This may be performed on the remote system 104 where the system 104 may detect the stuck in traffic scenario. Based on this information, the remote system 104 may be able to change the audio settings within the vehicle 102 to a more calm or smoother genre of music such as jazz. The music settings may be changed through over the air updates, adjusting the music on a server side for streaming services, etc.

The vehicle data may also be processed on the remote system 104 to autonomously pull the driver out of this environment into a more pleasant scenery. For example, and depending on the driver's state, the autonomous takeover system 366 may be given full control of the vehicle 602. The system 366 may reset a destination and then autonomously drive to that destination. The instructions for setting the destination may be provided by the remote system 104 through the network 108. A message may be displayed to the driver that the vehicle 602 will be taken over by the system 366.

Modified automated driving functionalities may be adjusted in real time or in the future including future models or when the vehicle 602 has uploaded new software. To adjust to the traffic jam scenario, for example, modified functionalities may include increased or decreased distances between the vehicles 604, 606, 608, 610, 612 and 614. Other types of adjustments may be made such as taking over the vehicle so that the user can concentrate on other things in the vehicle 602. This may occur in real time. Other vehicles 604, 606, 608, 610, 612 and 614 may adjust their behavior as well when connected to the remote system 104.

FIG. 7 is a schematic diagram of an exemplary vehicle 702 showing an aggressive driver retrieving data from a number of different gathering systems 336 and control systems 346 in accordance with one aspect of the present disclosure. Vehicle data may be collected or stored on the vehicle 702. This data may be the same or different from the vehicle data described above collected from the different systems 336 and 346 including information about the other vehicles 704, 706, 708, 710 and/or 712. For example, how close the driver gets to other vehicles, vehicles in the area, how slow other vehicles are or how many lanes are switched and in what time frame may be captured as vehicle data. In the scenario, the driver may narrowly miss vehicles 704 and 710 along their aggressive path 714.

The physiological system 368 may detect the aggressive driving behavior through a number of systems. Aggressive behavior may be defined as unsafe driving behavior performed deliberately. Speeding in traffic and tailgating are forms of aggressive driving behavior. As shown, aggressive behavior may be defined on how close the driver comes to other vehicles 704, 706, 708, 710 and/or 712 in their environment. Narrow misses of the vehicles 704, 706, 708, 710 and/or 712 may be an example of the driver's aggressive behavior. A number of lane changes between a period of time may also indicate a level of aggressiveness. Each of these characterize the driver's mentality.

Vehicle data that may be gathered from the sensors 504, 506, 508, 510, 512, 514, 516, 518 and/or 520 as the driver goes along their path 714 may include distances, speed and/or other information regarding the vehicles 704, 706, 708, 710 and/or 712. The distances and/or speed of the vehicles 704 and/or 706 may be captured by sensors 508, 510 and/or 512 of the vehicle 702. As the vehicle 702 continues its path 714, sensors 504, 506, 508 and/or 510 may be used to detect distances and/or speed of the vehicles 706 and/or 708. Narrowly missing vehicles 712 and/or 710, distances and/or speed may be captured by sensors 508, 510 and/or 512. More or less vehicle data may be captured through the different systems 336 and 346 and the vehicle data described taken along the path 714 is provided for illustrative purposes.

Facial expressions or voice inflections of the aggressive driver may be detected and trigger the sending of vehicle data. On the remote system 104, driving functionalities may be adjusted and provided to the vehicle 702, for example, adjusting autonomous driving based on the driver's schedule. Data may be streamed back to the vehicle 702, assuming that this is an autonomous vehicle. Future vehicles may use this vehicle data by determining what is appropriate behavior for autonomous vehicles when they lane change or go between vehicles 704, 706, 708, 710 and/or 712.

FIG. 8 is a schematic diagram of an exemplary vehicle 802 yielding to an emergency vehicle 812 that retrieves data from a number of different gathering systems 336 and control systems 346 in accordance with one aspect of the present disclosure. Vehicle data that may be captured or monitored may include external sound data. The sensors 504, 506, 508, 510, 512, 514, 516, 518 and/or 520 of the vehicle 802 may be used to receive vehicle data including distances, speed and/or movements of the other vehicles 804, 806, 808 and/or 810. For example sensors 508, 510 and/or 512 may be used to detect vehicles 806, 808 and/or 810 pulling to the side for the emergency vehicle 812.

The collected vehicle data may then be provided to the remote system 104 after a physiological event is detected. For example, the driver may be detected as nervous through cameras pointed at them. A number of points on the user's face may be detected to determine whether the driver is nervous. Further examples of how to detect facial expression will be described below.

After receiving the vehicle data, the remote system 104 may provide modifications such that the vehicle 802 may be pulled to the side allowing the emergency vehicle 812 to pass without any driver control. The autonomous takeover system 366, described above, may be given control. The provided vehicle data may allow the remote system 104 to determine whether it would be safe for the vehicle 802 to pull over.

FIGS. 6 through 8 presented above provided scenarios for which the vehicles 602, 702 and 802 collected vehicle data within real world driving scenarios. The first scenario presented a traffic jam with automated functionalities changing distances, locations or audio. The second scenario presented showed an aggressive driver and adjustments made to driving paths. Scenario three presented an emergency and adjusting driving functionalities to pull to the side. These scenarios should not be construed as limiting. Rather they are examples, and multiple combinations may be made that take in vehicle data, trigger the data to be sent to the remote system 104 and processed for modifying automated driving functionalities.

Figure 9:
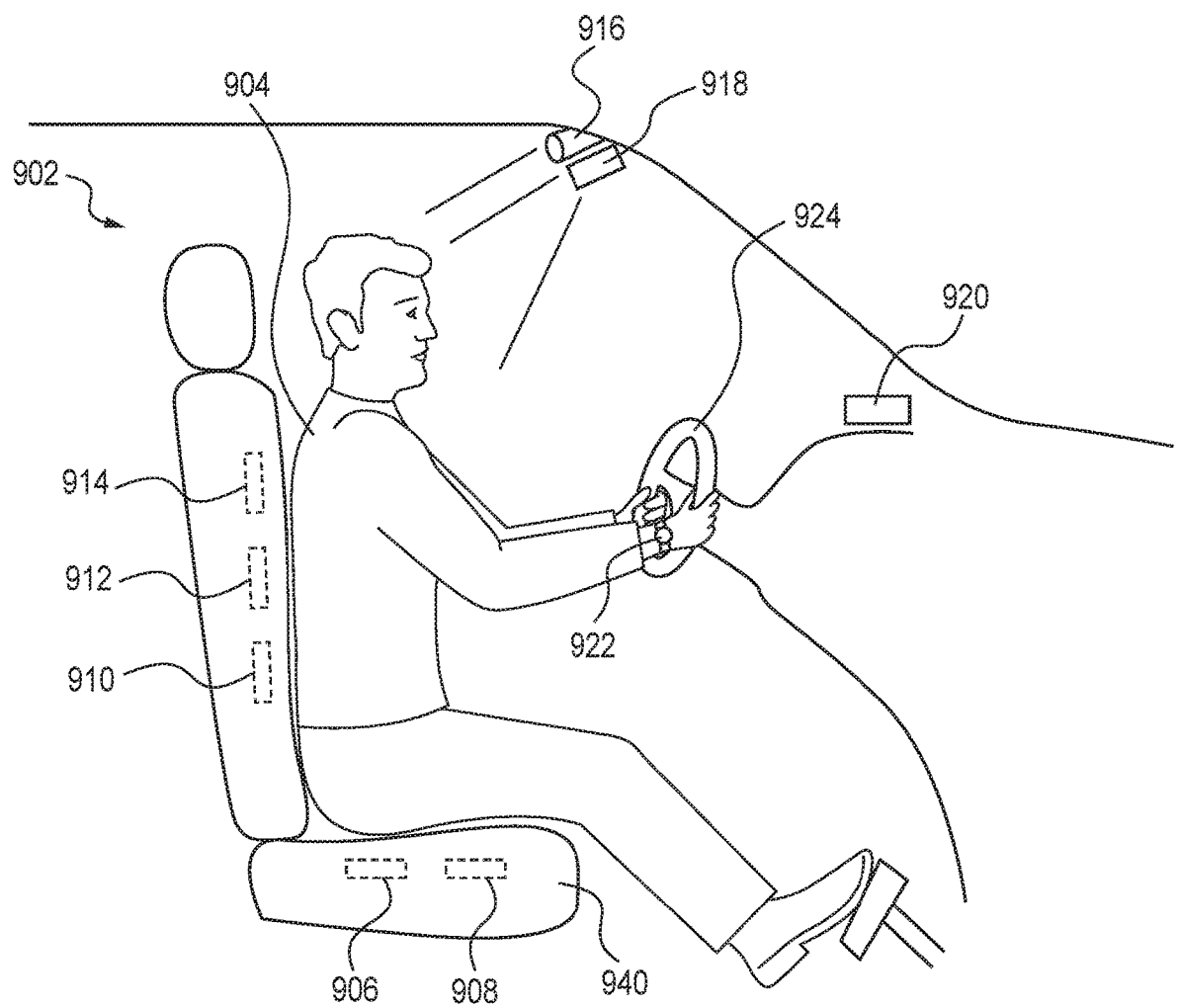
FIG. 9 is an illustrative schematic diagram showing exemplary physiological systems within a vehicle for determining an event in accordance with one aspect of the present disclosure.

Turning now to FIG. 9, an illustrative diagram showing exemplary physiological systems 368 within a vehicle 902 for determining an event in accordance with one aspect of the present disclosure is provided. The physiological event may be determined by the computing device 302, wearable device 390 or in-vehicle computing system 320. This event may be used as the trigger to provide vehicle data to the remote system 104 so that it may modify or change automated driving functionalities. The wearable device 390 may provide the event to the computing device 302, in-vehicle computing system 320 or to the remote system 104.

The physiological systems 368 may include seat sensors 370. These sensors 370 may also be part of the temperature sensors 372, skin sensors 378 or heart sensors 380. In one embodiment, seat sensors 906 and/or 908 may be placed in the bottom area of the seat 940. These sensors 906 and/or 908, may also detect leg movements or gestures as described above to detect a physiological event. In one example, a lower seat sensor 910, middle seat sensor 912 and higher seat sensor 914 may be used. These seat sensors 906, 908, 910, 912 and/or 914 within the seat 940 may provide the information to the computing device 302, in-vehicle computing system 320 wearable device 390 or to the remote system 104.

A microphone 916, or an array of them, may be provided in the vehicle 902 to detect a physiological event. The microphone 916 may be part of the vehicle 902 however the computing device 302 or watch 922 may include the microphone. The microphone 916, as part of the voice sensors 374, may be placed anywhere in the cabin of the vehicle 902. Inflections in the voice of the driver 904 may be detected through the microphone 916 for which FIG. 12 will provided more details.

Cameras 918 and/or 920 may be used as part of the temperature sensor 372, voice sensor 374, facial sensor 376, skin sensor 378 or heart sensor 380. In one embodiment, multiple cameras may be used to provide depth of an image. From this, the cameras may be used to detect different triggers. While the cameras 918 and/or 920 are shown at differing height levels, they may also be placed on the dashboard or other location.

As shown in FIG. 9, the wearable device 390 may come in the form of a watch 922 worn by the driver 904. The watch 922 may detect information related to the temperature sensor 372, voice sensor 374, facial sensor 376, skin sensor 378 or heart sensor 380. The watch 922 may communicate the information received to a device or process the information locally to detect an event to trigger uploading of the vehicle data to the remote system 104.

A steering wheel 924 may be part of the temperature sensor 372, voice sensor 374, facial sensor 376, skin sensor 378 or heart sensor 380. The sensor placed into the steering wheel 924 may located at a top, side or bottom portion of the wheel 924. In one embodiment, the same type of sensors may be placed on a shift lever where often times the driver 904 places their hand while driving.

While a number of sensors were provided in the vehicle 902, others may be used and are not limited to those described. These sensors were used to determine a physiological event thus triggering the upload of vehicle data to the remote system 104. Below, a number of examples will be provided that show how an event is detected.

FIGS. 10A and 10B show illustrative charts 1002 and 1004 for depicting a normal and stressed physiological state using the driver's heart rate in accordance with one aspect of the present disclosure. Heart sensors 380 within the physiological systems 368 may be used to detect the heart rate by measuring beats per minute. Cameras 918 or 920 may determine this measurement. Alternatively, seat sensors 370 may be used, or any other device described above. In one example, wearable devices 390, for example the watch 922, may be used to detect the heart rate of the driver 904.

In the first chart 1002, shown in FIG. 10A, regular patterns of heart beats are shown through a smooth waveform. Software or applications executed on the computing device 302 (application 308), wearable device 390 (application 398) or operations 322 (application 328) within the in-vehicle computing system 320 may be used to determine whether a normal heart rate is occurring. When a normal heart rate is detected, typically vehicle data may not be provided to the remote system 104. A normal heart rate may have slight increases or decreases in the beats per minute.

In the second chart 1004, shown in FIG. 10B, a waveform of a heart rate that shows that the driver 904 may be stressed is provided. The waveform of a stressed driver may be characterized in erratic jumps. In one embodiment, an appropriate amount of time may elapse before sending the vehicle data to the remote system 104. The time period may be used to remove any inaccurate readings through the heart monitors. Alternatively, the vehicle data may be sent regardless of time period such that when it is detected the vehicle data is automatically sent. Different measurements in the heart rate may be related to different physiological states, for example, the driver may be upset, tired, lonely, etc. Each of these states may be used for providing different types of vehicle data to the remote system 104.

In the example shown, the driver's beats per minute increases at points 1006, 1008 and 1010. These may be periods where the driver's stress level may trigger the sending of vehicle data to the remote system 104. In one embodiment, a threshold 1012 may be implemented such that not all increases in heart beats per minute qualify as a physiological event. For purposes of illustration, the threshold 1012 may be set at eighty beats per minute. Point 1006 may be below the threshold 1012 and no vehicle data would be sent. Points 1008 and 1010, however, which are above the threshold 1012 may qualify as a physiological event. The threshold 1012 would thus allow sending of vehicle data twice.

FIG. 11 is an illustrative chart 1102 showing an increase temperature of the driver depicting a physiological event in accordance with one aspect of the present disclosure. Temperature sensors 372 may be used in the seat 940, steering wheel 924, or as detected by cameras 918 and 920, for example. An initial reading on the driver's temperature may be taken into account. Increases in temperature based off the base reading may indicate a physiological event as shown in chart 1102.

Temperature increases may be due to the driver 904 becoming angry or volatile. Decreases in temperature may also be monitored for other events such as the driver falling asleep. Increases or decreases in temperature may trigger a physiological event. In one embodiment, HVAC systems may be taken into account to determine whether the temperature of the driver 904 is actually increasing or decreasing.

In the example shown, a threshold 1106 may be set at nine-eight point nine degrees Fahrenheit. A physiological event may not occur until it reaches above the threshold 1106. For example, at point 1104, the driver's temperature reaches the threshold 1106. At this point 1104, vehicle data is provided to the remote system 104. An event may also occur at a lower threshold such that a driver's temperature may dip below a certain temperature. Typically, this may result from a driver falling asleep or less coherent.

FIG. 12 is an illustrative chart 1202 showing a voice inflection depicting a physiological event in accordance with one aspect of the present disclosure. The microphone 916 in the vehicle 902 may be used to capture voice data within the cabin. Inflections in the voice may be tagged as a physiological event. For example, and as shown in the chart 1202, a higher inflection may trigger an event. If the inflections reach above a threshold line 1204 than an event may be triggered such that vehicle data would be sent to the remote system 104. In the example shown, at point 1206, the inflections are above the threshold 1204 triggering vehicle data to be sent to the remote system 104. In one embodiment, inflections are not used to determine an event. Rather, keywords, such as curse words, may be used to trigger the event.

FIG. 13 provides exemplary facial expressions to show different physiological states of a driver 904 in accordance with one aspect of the present disclosure. Cameras 918 and 920 (facial sensors 376) may be used to determine facial expressions. For example, in the first driver 1302, the driver is perspiring and is unhappy. This may cause a trigger and vehicle data would be sent up to the remote server 104. The trigger may result from a detection of the facial expression for a threshold period of time, or for example, multiple emotions are detected on the driver's face.

The second driver 1304 may be happy and nothing would be sent up. The third driver 1306 may be detected by the cameras 918 and 920 (facial sensors 376) as intoxicated or some other non-coherent state. This may cause an event to be triggered to send vehicle data. The trigger may be provided based on a number of determinations that the driver is intoxicated, for example, the driver's eyes are dilated and/or slower facial emotions.

Figure 14:
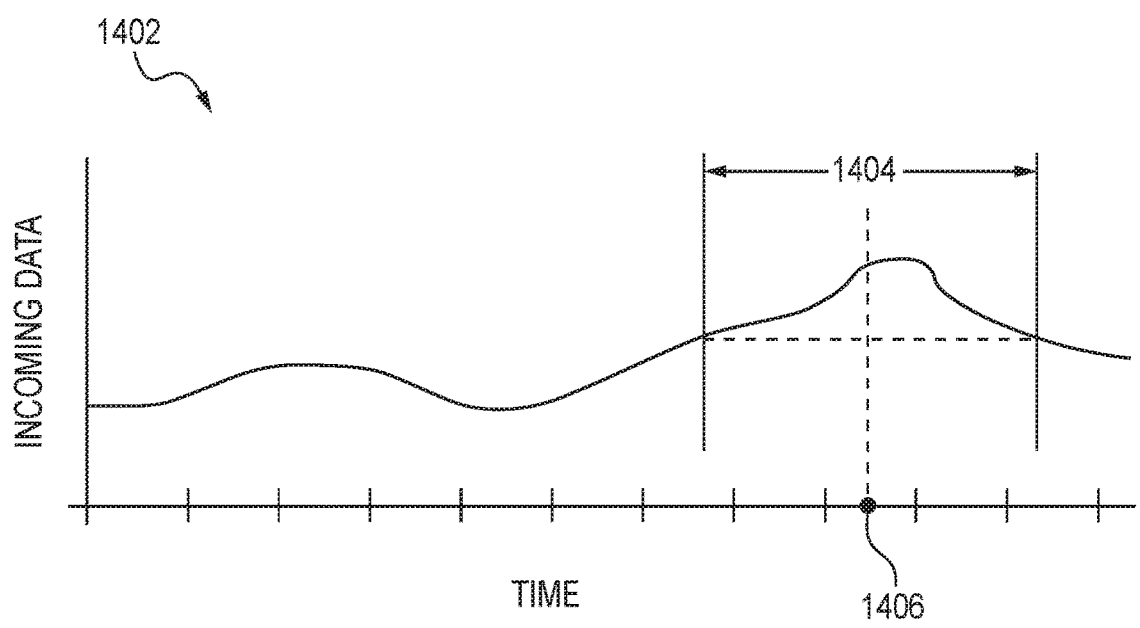
FIG. 14 is an illustrative chart showing a creation of a data window based on a physiological event in accordance with one aspect of the present disclosure.

After a physiological event has been detected, vehicle data may be sent to the remote server 104 for modifying automated driving functionalities. All vehicle data or selected vehicle data may be sent. The selected vehicle data may be based on the physiological event detected. FIG. 14 is an illustrative chart 1402 showing a creation of a data window 1404 based on a physiological event in accordance with one aspect of the present disclosure. At the point 1406 where the physiological event is detected, the window 1404 may be created by taking the vehicle data within plus or minus a time period before and after the point 1406. The time period may be equal in taking data before and after the point 1406. Alternatively, more vehicle data may be taken after the point 1406 or before the point 1406.

In one embodiment, the time frame may vary dependent on which type of physiological event was triggered. For example, if the triggering event is based on facial expressions indicating that the driver is aggressive, more vehicle data may be uploaded to the remote system 104. More vehicle data may be required as the time frame of the event is longer. In another example, short bursts of vehicle data may be provided when voice inflections are detected. If a number of bursts are made in a row within a predetermined time, a longer data window 1404 may be generated. Vehicle data may be stored in the vehicle data storage device 334 such that the data may be retrieved and not lost. These windows 1404 may be sent to the remote system 104.

Figure 15:
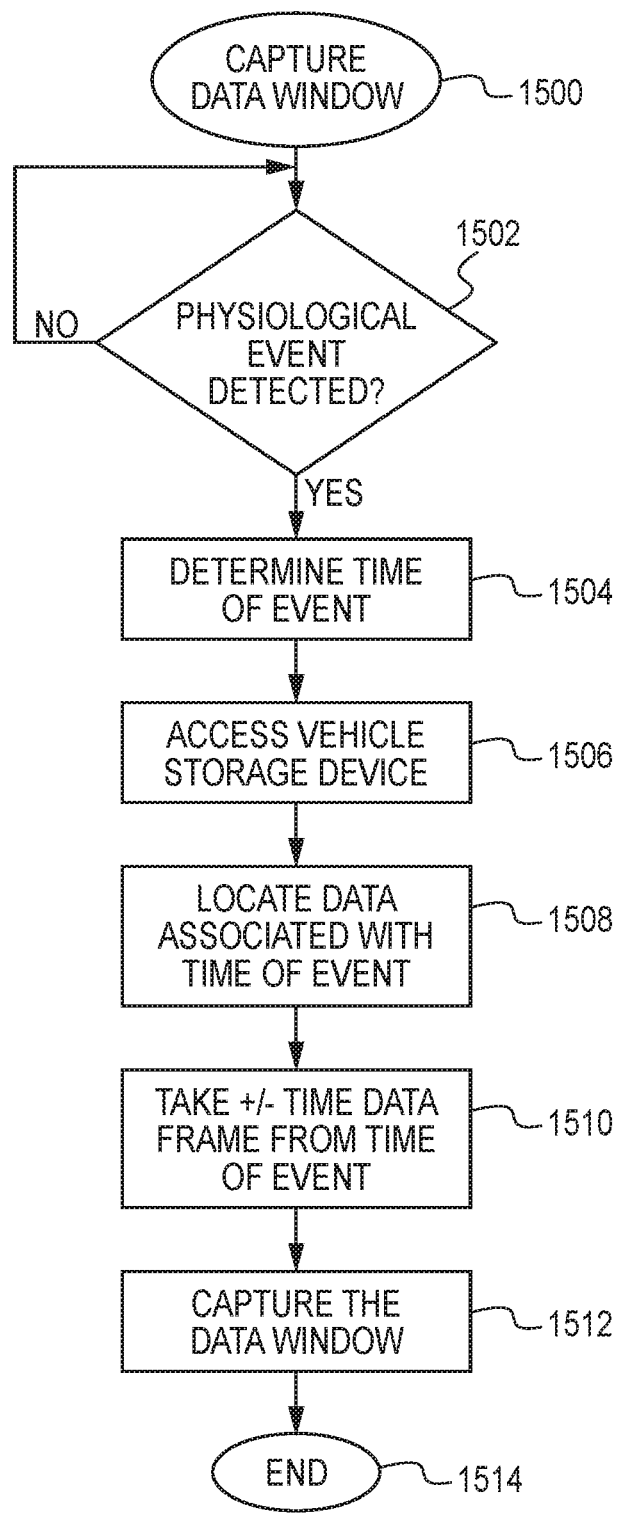
FIG. 15 is an exemplary flow chart showing capturing data within a window when a physiological event is detected in accordance with one aspect of the present disclosure.

FIG. 15 is an exemplary flow chart showing capturing data within a window 1404 when a physiological event is detected in accordance with one aspect of the present disclosure. Fewer or more processes may be provided within the flow chart, and those shown should not be construed as limiting. The processes may begin at block 1500. A number of variants for capturing data to be sent to the remote system 104 have been described above and the flow chart presented herein is one illustration, but is not limiting.

At decision block 1502, a physiological event determination is made. For example, and as shown above, the heart rate of the driver may be determined and if variations exist showing a stressed heart rate, a physiological event may be triggered. Increases or decreases in the driver's temperature may also indicate an event. Inflections in voice patterns may cause the event to occur. Facial monitoring may be used to also determine an event. As discussed above, different physiological events may trigger sending different vehicle data to the remote system 104, in one embodiment. Alternatively, the trigger may cause all vehicle data to be sent during the time the event was detected in the window 1404 or variants described above.

When no physiological event is detected, the processes continue at decision block 1502. However, and when an event has been detected, the time of the event is determined at block 1504. The vehicle data when it is received may be tagged with time data, as described above, and the physiological event may be tagged with the same time data.

At block 1506, vehicle data may be accessed. This may include retrieving data within the vehicle data storage device 334. In one embodiment, instead of retrieving the data, the vehicle data may be sent once the physiological event has been created. The vehicle data, in this embodiment, may be provided for a period of time depending on the event detected. At block 1508, the vehicle data associated with the time of the event may be located.

To create data window 1404, at block 1510, a time frame is taken which includes a plus or minus time from the time of event. This vehicle data may show information which may be pertinent before the event was detected. As described above, the plus or minus time period does not have to be the same and may vary depending on the physiological event detected, how long the event lasts, the repetitiveness of the event, etc.

At block 1512, the vehicle data is captured in a window 1404. The data may be further refined or processed, for example, depending on the triggering event, the data may be refined to include data related to the event. Vehicle data related to some control systems 346 may not be relevant when the event indicates that only vehicle data from gathering systems 336 are used. In one example, an event caused by a heart rate increase may not require vehicle data from the audio system 348 to modify automated driving functionalities. The processes may end at block 1514.

To further elaborate on selecting vehicle data based on the physiological event detected, FIG. 16 is an illustrative table depicting gathering and control system data to be uploaded based on detected physiological events in accordance with one aspect of the present disclosure. These examples are provided for illustrative purposes and should not be construed as limiting, rather they should represent examples to clarify the selection of vehicle data to be sent to the remote system 104 based on the event detected. The physiological event may be sent with the vehicle data.

In one example, and as shown at the top of the table, a normal heart rate may typically not result in sending vehicle data from either the gathering system 336 or control systems 346. By not providing the vehicle data, data usage may be reduced.

In the next example, when the driver's heart rate shows a stressed state, then different types of vehicle data may be sent to the remote system 104. The vehicle data may be captured in a window 1404 as described above. Representative vehicle data from the gathering systems 336 may include data from optical, audio and/or positional sensors. These may include cameras 338, lidar and/or radar 340, microphone 342 or GPS 344. This type of vehicle data may be relevant for modifying automated vehicle functions to understanding the scene and why the driver is stressed. Vehicle data from the control systems 346 may include data from the telecommunication system 352, steering system 354, blind spot system 356 and collision warning system 358. These systems may be potentially reasons why the driver's heart rate increased and so modifying automated driving functions may use this data.

In the next example, a temperature increase physiological event may result in vehicle data from the optical, audio and/or location sensors, such as cameras 338, lidar and/or radar 340 or GPS 344 from the gathering systems 336, to be sent to the remote system 104. This vehicle data may be used for environmental understanding. Vehicle data from the control systems 346 that may be sent include data from the climate control system 350, steering system 354, blind spot system 356, collision warning system 358 or acceleration/braking system 362. This vehicle data may be used to determine why the driver's temperature increased and to modify functions based on the vehicle data.

In the next example, when a physiological event is retrieved from the voice inflection, vehicle data from the gathering systems 336 including data from the microphone 342 may be sent to the remote system 104. This may be used to determine specific words within the voice stream. Vehicle data from the control systems 346 may be also sent such as data from the telecommunication system 352. This may be used to modify functionalities by determining the amount of bandwidth the driver is using.

Facial expressions may also be monitored to trigger vehicle data to be sent to the remote system 104. In the next example, when the driver has been detected as nervous, vehicle data from the gathering systems 336 including data from the camera 338 and GPS 344 may be sent. This information may indicate where the driver is and their driving environment. Furthermore, when the driver has been detected to be nervous, vehicle data from the control systems 346, including data from the telecommunication system 352, steering system 354, blind spot system 356, collision warning system 358, acceleration/braking system 362 or lane assist system 364, may be provided. These control systems 346 may provide vehicle data relevant to why the driver was nervous and the remote system 104 may be able to modify automated driving functionalities using this data.

In the next example, when the driver is happy, generally no data may be sent to the remote system 104. As no physiological event is occurring, there is no data sent up. In the next example, when the driver has been detected as intoxicated, vehicle data from the gathering system 336 including data from the GPS 344 may be sent. On the remote system 104, functionalities may be changed such that control systems 346 are taken control of and the driver may be taken off the road, for example.

Figure 17:
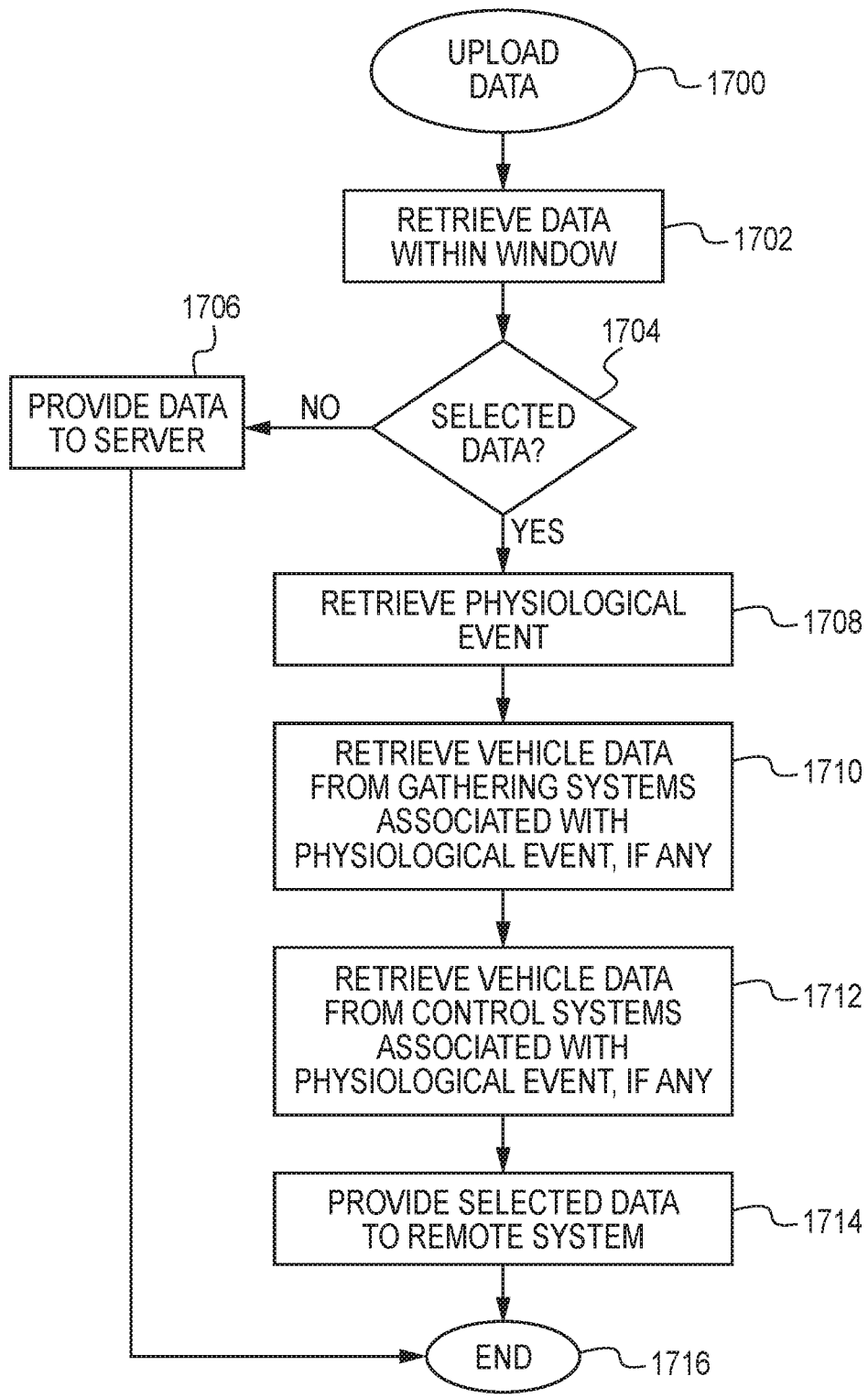
FIG. 17 is an exemplary flow chart showing selective uploading data when a physiological event has been detected in accordance with one aspect of the present disclosure.

As shown above, selected vehicle data may be provided from the vehicle 102 to the remote system 104 based on the physiological event detected. However, and in accordance with some embodiments, all vehicle data may be provided and processed on the remote system 104. FIG. 17 is an exemplary flow chart showing selective uploading data when a physiological event has been detected in accordance with one aspect of the present disclosure. The processes provide one example and should not be construed as limiting.

The processes may begin at block 1700. At block 1702, vehicle data may be retrieved within a window 1404, as described above. For example, depending on the time of the detected physiological event, a window 1404 may be created to capture information before and after the event. This may include taking more or less data at the beginning of the time of the event or after the event. Alternatively, vehicle data may be retrieved after the event was detected.

At decision block 1704, a determination is made to determine whether certain data should be selected based on the physiological event. In some instances, all data may be sent as the event is undiscernible and rather the event should be parsed on the remote system 104. At block 1706, and when data should not be selected, all the vehicle data is provided to the remote system 104 and the processes end at block 1716.

On the other hand, and if vehicle data is to be selected at decision block 1704, the type of physiological event is retrieved at block 1708. As shown above, the physiological event may determine which type of vehicle data should be sent to the remote system 104. At block 1710, vehicle data from the gathering system 336 may be retrieved, if any. This information may be retrieved from the vehicle data storage device 334, or other location. Continuing with the physiological event of a nervous detection, vehicle data from the camera 338 and GPS 344 may be retrieved. This information may indicate where the driver is in their environment.

At block 1712, vehicle data from the control systems 346 may be retrieved, if any. Furthermore, when the driver has been detected to be nervous, vehicle data from the telecommunication system 352, steering system 354, blind spot system 356, collision warning system 358, acceleration/braking system 362, lane assist system 364 may be sent. Any of these control systems 346 may provide information relevant to why the driver was nervous.

The vehicle data may then be provided to the remote system 104 at block 1714. This may include opening a communication channel with the network 108 or providing the selected vehicle data over an already opened channel. The processes may end at block 1716.

The data structures and code, in which the present disclosure may be implemented, may typically be stored on a non-transitory computer-readable storage medium. The storage may be any device or medium that may store code and/or data for use by a computer system. The non-transitory computer-readable storage medium includes, but is not limited to, volatile memory, non-volatile memory, magnetic and optical storage devices such as disk drives, magnetic tape, CDs (compact discs), DVDs (digital versatile discs or digital video discs) or other media capable of storing code and/or data now known or later developed.

The methods and processes described in the disclosure may be embodied as code and/or data, which may be stored in a non-transitory computer-readable storage medium as described above. When a computer system reads and executes the code and/or data stored on the non-transitory computer-readable storage medium, the computer system performs the methods and processes embodied as data structures and code and stored within the non-transitory computer-readable storage medium. Furthermore, the methods and processes described may be included in hardware components. For example, the hardware components may include, but are not limited to, application-specific integrated circuit (ASIC) chips, field-programmable gate arrays (FPGAs) and other programmable-logic devices now known or later developed. When the hardware components are activated, the hardware components perform the methods and processes included within the hardware components.

The technology described herein may be implemented as logical operations and/or components. The logical operations may be implemented as a sequence of processor-implemented executed blocks and as interconnected machine or circuit components. Likewise, the descriptions of various component components may be provided in terms of operations executed or effected by the components. The resulting implementation is a matter of choice, dependent on the performance requirements of the underlying system implementing the described technology. Accordingly, the logical operations making up the embodiment of the technology described herein are referred to variously as operations, blocks, objects or components. It should be understood that logical operations may be performed in any order, unless explicitly claimed otherwise or a specific order is inherently necessitated by the claim language.

Various embodiments of the present disclosure may be programmed using an object-oriented programming language, such as SmallTalk, Java, C++, Ada or C #. Other object-oriented programming languages may also be used. Alternatively, functional, scripting and/or logical programming languages may be used. Various aspects of this disclosure may be implemented in a non-programmed environment, for example, documents created in HTML, XML or other format that, when viewed in a window of a browser program, render aspects of a GUI or perform other functions. Various aspects of the disclosure may be implemented as programmed or non-programmed elements or any combination thereof.

The foregoing description is provided to enable any person skilled in the relevant art to practice the various embodiments described herein. Various modifications to these embodiments will be readily apparent to those skilled in the relevant art and generic principles defined herein may be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. A vehicle having at least one automated driving functionality comprising:
   at least one sensor detecting a physiological event of a driver; and a processor configured to:
  in response to detecting the physiological event, determine a time frame for the detected physiological event and which vehicle data from one or more of a plurality of systems to transmit to a remote system;
  capture a data window including the vehicle data that is related to the physiological event during the time frame, wherein the vehicle data is selected based on a type of the detected physiological event;
  transmit, via an interface, the captured data window and information associated with the physiological event to the remote system;
  receive, via the interface and from the remote system, at least one modification to the at least one automated driving functionality, the at least one modification being based on the captured data window and the information associated with the physiological event; and
  adjust the at least one automated driving functionality based on the least one modification received from the remote system.

2. The vehicle of claim 1, wherein the at least one sensor is in a wearable device.

3. The vehicle of claim 1, wherein the at least one sensor is a seat sensor, temperature sensor, voice sensor, facial sensor, skin sensor or heart sensor.

4. The vehicle of claim 1, wherein the physiological event is detected by a driver's heart rate, temperature, voice inflection or facial expression.

5. The vehicle of claim 1, wherein the determined vehicle data is received from a camera, lidar/radar, microphone or global positioning system.

6. The vehicle of claim 1, wherein the determined vehicle data is received from an audio system, climate control system, telecommunication system, steering system, blind spot system, collision warning system, cruise control system, acceleration/brake system, lane assist system or autonomous takeover system.

7. The vehicle of claim 1, wherein the at least one modification to the at least one automated driving functionality comprises adjustments to a distance in an adaptive cruise control system.

8. The vehicle of claim 1, wherein the at least one modification to the at least one automated driving functionality comprises adjustments to a parameter defining a level of aggressive driving style.

9. A method for transmitting vehicle data to a remote system comprising:
  detecting a physiological event using one or more sensors;
  in response to detecting the physiological event, determining, using a processor, a time frame for the detected physiological event and which vehicle data from one or more of a plurality of systems to transmit to a remote system external to the vehicle;
  capturing a data window including the vehicle data that is related to the physiological event during the time frame, wherein the vehicle data is selected based on a type of the detected physiological event
  transmitting, via an interface, the captured data window and information associated with the physiological event to the remote system;
  receiving, via the interface and from the remote system, at least one modification to at least one automated driving functionality of a vehicle, the at least one modification being based on the captured data window and the information associated with the physiological event; and adjusting, using the processor, the at least one automated driving functionality based on the at least one modification received from the remote system.

10. The method of claim 9, wherein detecting the physiological event comprises determining a heart rate of a driver, the physiological event occurring when the heart rate is above a threshold.

11. The method of claim 9, wherein detecting the physiological event comprises determining a temperature of a driver, the physiological event occurring when the temperature is higher or lower than a threshold.

12. The method of claim 9, wherein detecting the physiological event comprises determining a voice inflection of a driver, the physiological event occurring when the voice inflection is higher than a threshold.

13. The method of claim 9, wherein detecting the physiological event comprises determining a facial expression of a driver, the physiological event occurring when the facial expression is unhappy or intoxicated.

14. The method of claim 9, wherein transmitting the determined vehicle data and the information associated with the physiological event to the remote system comprises sending the determined vehicle data and the information associated with the physiological event directly from an in-vehicle computing system or indirectly from a computing device connected to the in-vehicle computing system.

15. An in-vehicle computing system comprising:
  a physiological sensor;
  at least one processor; and
  a memory operatively coupled to the processor, the memory storing program instructions that when executed by the processor, causes the processor to:
  detect an physiological event of a driver through the physiological sensor;
    in response to detecting the physiological event, determine a time frame for the detected physiological event and which vehicle data from one or more of a plurality of systems to transmit to a remote system;
    capture a data window including the vehicle data that is related to the physiological event during the time frame, wherein the vehicle data is selected based on a type of the detected physiological event
    transmit, via an interface, the captured data window and information associated with the physiological event to the remote system;
    receive, via the interface, at least one modification from the remote system to adjust an automated driving functionality, the at least one modification being based on the captured data window and the information associated with the physiological event; and
    adjust the at least one automated driving functionality based on the least one modification received from the remote system.

16. The in-vehicle computing system of claim 15, wherein the determined vehicle data within the data window comprises selected vehicle data based on the physiological event.

17. The in-vehicle computing system of claim 15, wherein the physiological event is detected from the driver's heart rate, temperature, voice inflection or facial expression.

18. The in-vehicle computing system of claim 15 wherein adjusting the automated driving functionality comprises taking over control of a vehicle.

19. The in-vehicle computing system of claim 15, wherein adjusting the automated driving functionality comprises modifying a distance between vehicles on an adaptive cruise control system.

20. The in-vehicle computing system of claim 15, comprising a wearable device having the physiological sensor.

21. The method of claim 9, wherein a length of the time frame varies based on the type of the detected physiological event detected and an amount of the determined vehicle data to transmit varies based on the length of the time frame.

22. The method of claim 9, wherein the determined vehicle data is related to the detected physiological event and is selected from a subset of the plurality of systems.

* * * * *